US006062691A

United States Patent [19]

Markson

[11] Patent Number: 6,062,691

[45] Date of Patent: May 16, 2000

[54] SYSTEM KIT AND METHOD FOR REDUCING OCULAR DISCOMFORT AND VISION PROBLEMS ASSOCIATED WITH SUSTAINED CLOSE-RANGE VIEWING

[76] Inventor: Jeffrey Markson, 244 Longhouse La., Slingerlands, N.Y. 12159

[21] Appl. No.: 09/294,460

[22] Filed: Apr. 19, 1999

[51] Int. Cl.[7] ........ A61B 3/00

[52] U.S. Cl. ........ 351/203; 601/37

[58] Field of Search ........ 351/41, 200, 203; 128/745; 601/23, 37

[56] References Cited

U.S. PATENT DOCUMENTS

| | | | |
|---|---|---|---|
| 1,464,075 | 8/1923 | Hull | 351/203 |
| 2,837,086 | 6/1958 | Thorburn | 351/203 |
| 4,294,522 | 10/1981 | Jacobs | 351/203 |
| 5,812,239 | 9/1998 | Eger | 351/203 |

*Primary Examiner*—Huy Mai
*Attorney, Agent, or Firm*—Adams & Wilks

[57] ABSTRACT

A system kit is provided for reducing ocular discomfort and vision problems associated with sustained close-range viewing of a video display terminal. The system kit comprises, in combination, eyewear for reducing the amount of accommodation or focusing required by eyes of an operator of the video display terminal in order to see the video display terminal at close range, at least one visual therapy device to enable the operator to perform ocular exercises to improve eye muscle control, and an information display and a record medium providing information for improving ergonomic conditions while viewing the video display terminal and instructions on how to use the eyewear and the visual therapy device. The combination of the eyewear, the visual therapy device, the visual display and the record medium enable the reduction of ocular discomfort and vision problems associated with sustained close-range viewing of the video display terminal.

38 Claims, 10 Drawing Sheets

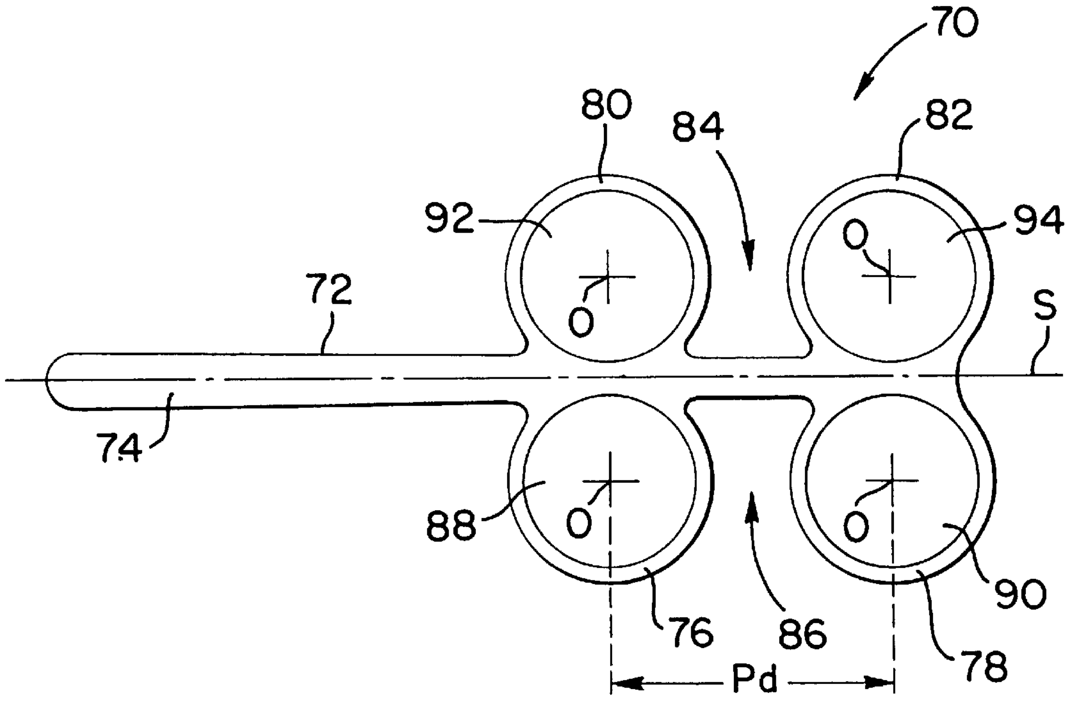
F/G. 6
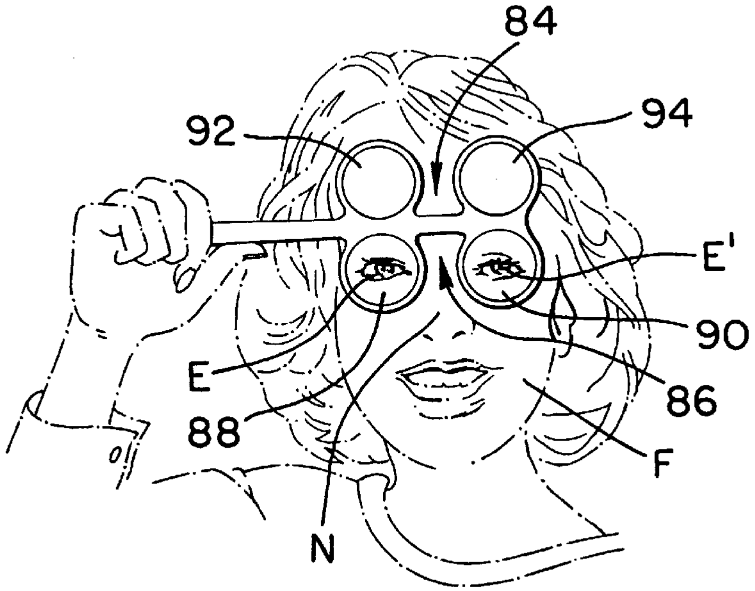
F/G. 7

B L I N K

Room Lighting
▪Dim room lights to equal monitor brightness, especially those in front of and above computer.
▪Cover windows with shades and close doors.
▪Doors and windows should be to the sides of computer user, not in front of or behind.
▪Direct all fluorescent light sources away from monitor.

Glare/Reflections
▪Use anti-glare monitor cover made of glass or high quality plastic.
▪Computer glasses have anti-glare coating.

Dry Eyes
▪Make sure to blink more often while using a computer. Normal blink rate is 12-15 times/minute.
▪Use eye drops - artificial tears - before they feel dry.
▪Only rub eyes very gently.
▪Make sure no vent is blowing directly at you.
▪Close eyes - gently role you finger downward along upper eyelid. This releases oil to help your tears from evaporating as you stare.
▪Tap a finger gently on your forehead. This stimulates the nerves to produce more tears.

Computer Position
▪Distance for viewing monitor should be from 18 to 30 inches.
▪Top of monitor should be slightly below user's eye level.
▪Bottom of monitor should not be more than 40% eye level
▪Adjust height for keyboard so that user's elbow is at right angles.
▪Adjust workstation furniture for proper posture.
▪Use chair having a straight back with support.
▪Feet should be raised slightly.

Monitor
▪Use a high resolution, high quality monitor.
▪Clean monitor regularly with non-ammonia cleaner to reduce static.
▪Use anti-glare screen to decrease reflections and increase contrast.
▪Adjust contrast to reduce discomfort.
▪Adjust color using comfort color determinator chart to find your best color combination.
▪Adjust brightness - monitor brightness should equal the room brightness.
▪Adjust font size.

Tips for Reducing "Computer Vision Syndrome"
▪Yearly eye exams are very important.
▪Use computer glasses to reduce effects of eyestrain, headaches, fatigue and blurring of vision.
▪Place document holder at the same distance from you as the monitor.
▪Take breaks to relax eye muscles. For 5 minutes each hour, look far away and do not try to see things clearly.
▪Strengthen eye muscles - perform visual therapy exercises to strengthen both the pointing muscles and the focusing muscles.
▪Contact lenses are not recommended for computer use because they tend to dry out and cause discomfort and blurring of vision which increase eyestrain.
▪Include UV protection while using a computer.

FIG. 10B

| | GENERAL COMFORT | CLARITY | HEADACHES |
|---|---|---|---|
| DAY 1<br>Letter Color:<br>Background. Color: | Good<br>Poor<br>Moderate | Clear<br>Slightly Blurred<br>Blurry | Yes<br>No |
| DAY 2<br>Letter Color:<br>Background Color: | Good<br>Poor<br>Moderate | Clear<br>Slightly Blurred<br>Blurry | Yes<br>No |
| DAY 3<br>Letter Color:<br>Background Color: | Good<br>Poor<br>Moderate | Clear<br>Slightly Blurred<br>Blurry | Yes<br>No |
| DAY 4<br>Letter Color:<br>Background Color: | Good<br>Poor<br>Moderate | Clear<br>Slightly Blurred<br>Blurry | Yes<br>No |
| DAY 5<br>Letter Color:<br>Background Color: | Good<br>Poor<br>Moderate | Clear<br>Slightly Blurred<br>Blurry | Yes<br>No |

FIG. 15

SYSTEM KIT AND METHOD FOR REDUCING OCULAR DISCOMFORT AND VISION PROBLEMS ASSOCIATED WITH SUSTAINED CLOSE-RANGE VIEWING

BACKGROUND OF THE INVENTION

1. Field of the Invention

The present invention relates generally to the reduction of ocular discomfort and vision problems associated with sustained close-range viewing, and more specifically to a system kit and method for use by a viewer to reduce eyestrain associated with sustained close-range viewing.

2. Background of the Invention

The use of computers in a variety of applications such as word processing, accounting, desk-top publishing, computer-aided drafting, engineering, programming, spreadsheets, game-playing and the like is now widespread. These applications demand sustained use of the computer for more hours than ever before and have raised concerns about undesirable health effects to the user. As computer usage in the workplace increases due to advances such as electronic mail, computer ordering/billing, Internet advertising, computer faxing, and on-line services, reducing an employee's computer-related fatigue plays an increasingly vital role in enhancing productivity.

Many computer users complain of ocular discomfort and vision problems, muscular tension, joint stress and strain, and neck soreness. The ocular discomfort and vision problems are generally referred to as Computer Vision Syndrome (CVS), while the muscle and joint (musculoskeletal) disorders are generally referred to as repetitive stress disorders. Repetitive stress injuries usually occur by performing repetitive movements or by being required to remain in a specific position for long periods of time.

While most health surveys for computer users clearly show that the majority of health related complaints are visually oriented, almost all public and professional attention has been directed towards the musculoskeletal disorders, such as carpal tunnel syndrome and neck tension disorder. According to a survey conducted by the National Institute for Occupational Safety and Health (NIOSH), about 88% of the people who work at computers for more than three hours a day suffer from symptoms of eyestrain. The same survey conducted by the NIOSH states that while up to 88% of computer users experience CVS, 22% of computer users experience repetitive stress disorders. It has been estimated that it costs $1.9 billion a year for U.S. companies and employees to diagnose and treat CVS.

Moreover, numerous ergonomic products are currently available to reduce or minimize the discomfort associated with prolonged computer use to prevent musculoskeletal disorders. These products are primarily directed to preventing carpal tunnel syndrome and muscle fatigue. However, these products do not provide prevention of eyestrain. Accordingly, there is a continuing need in the industry for a system for reducing eyestrain caused by prolonged computer use.

It is well known that ocular discomfort and vision problems, such as eyestrain, burning sensations in the eyes, headaches, fatigue, blurring of vision, decreased productivity, and the progressive increase in one's level of nearsightedness result from the prolonged viewing of computer monitor screens. Particularly, severe operator eyestrain results when the operator is required to view the monitor screen for extended periods of time while simultaneously operating a computer keyboard and periodically viewing various documents.

Vision problems and discomfort associated with prolonged viewing appear to be caused by strain of the eye muscles of the viewer attempting to maintain a sustained focus and to converge the eyes to the near point image on the screen. It has been determined that when an individual looks at a computer monitor screen, the natural position of the eye muscles directs the eyes almost straight ahead for distance vision. Therefore, in order to view a computer monitor, at the normal viewing distance of from 18–30 inches, the eye muscles strain as we focus and converge the eyes, then sustain this focus and convergence. When we gaze downward at about an angle of 20°–30°, the eyes will converge automatically for near vision.

In the course of developing the system kit and technique of the instant invention, applicant has formulated a new and unique theory which is believed to explain the cause of CVS. It is believed that there is a neurological "battle" occurring, which causes the eye muscles to fight against each other, and the resulting muscle spasm leads to problems relating to CVS. When we look at a monitor, we see light areas where the letters are located and dark areas everywhere else on the screen. Projecting these light and dark areas back to the retina, light causes the pupil to constrict, or get smaller, while dark areas cause the pupil to dilate, or get bigger. These opposing signals cause the opposing muscles, the dilator and the sphincter, to work at the same time, causing a muscle spasm which leads to eyestrain and resulting vision problems. As the computer user looks away from the monitor, the spasm prevents the eye from relaxing the focus and see in the distance, momentarily causing blurred vision. For a while, about 6–12 months, you can get the spasm to relax by closing the eyes and relaxing for a few moments. Eventually, however, the focus will not relax and the computer user becomes more nearsighted. It will be appreciated that the foregoing problems are generally unrecognized, especially when working with video display terminals.

The constant glare from the computer screen also often results in eyestrain, which leads to severe headaches and other discomforts. Reflections on the computer screen from overhead lights also contribute to eyestrain and fatigue. In addition, background and overhead lighting can produce glare in the computer operator's eyes which makes it difficult for the operator to focus on the computer monitor.

It has been proposed to reduce the level of background and overhead room lighting in order to reduce eyestrain. However, decreasing the surrounding room lighting is often not possible due to other workers, and is generally not beneficial as a computer user must still be able to look to and see other items and documents near the computer. It has also been proposed to increase the brightness and/or contrast settings on the monitor in order to overcome the effects of light striking the monitor surface. Such techniques are generally not favorable, however, because in addition to dramatically increasing the strain and fatigue on the user's eyes, the computer monitor may be damaged by burn-in, a common form of display damage.

In addition to eyestrain caused by attempting to focus on a computer monitor, persons using bifocals are forced to tilt their heads up toward the ceiling in order to view the screen through their bifocal segment. Tilting the head is uncomfortable and causes neckstrain, backache and fatigue.

Various types of optical apparatus have been proposed to alleviate or reduce such eyestrain by placing optical devices between the operator and the computer screen. For example U.S. Pat. No. 4,712,870 to Robinson describes a magnifying Fresnell lens which is interposed between the monitor and the operator to magnify the monitor screen image. Another such Fresnell magnifying lens and glare reduction system is disclosed in U.S. Pat. No. 4,577,928 to Brown. An anti-glare device comprising a filter screen for attachment to a CRT computer terminal display is disclosed in U.S. Pat. No. 4,253,737 to Thomsen. An adjustable lens holder for various magnifier, color tinting or anti-glare lenses is disclosed in the U.S. Pat. No. 4,529,268 to Brown.

Numerous anti-glare shields and eye shades have also been proposed for various purposes. For example, various eye shields have been proposed for drivers and pilots to reduce the glare from the sun or lights. Other eye shields have been proposed which serve as blinders to avoid distraction during various activities and for training exercises. Examples of these types of eye shields are disclosed in U.S. Pat. Nos. 2,933,734; 3,330,051; 3,308,498; 3,225,459 and 5,261,124. These devices do not provide adequate protection from glare and reflection from incidental light, as well as the glare from the computer terminal. Furthermore, these devices are typically bulky and uncomfortable to wear.

Although image magnification and glare reduction devices may provide certain benefits, the principal cause of computer operator eyestrain remains that the operator's eyes must converge and focus on the images carried by the CRT computer monitor screen. If the degree of focussing required to bring the screen into focus can be reduced, the resultant eyestrain is significantly reduced.

Another general eye discomfort of computer users is generally related to "dry eye". Recent studies by the medical profession have resulted in a breakthrough with respect to understanding the problem. Medical investigators have determined that a computer user staring at a display terminal blinks at a rate which is significantly below the norm for that individual. For example, the blink rate for computer users can drop from a normal of 12–25 times per minute to 3–5 times per minute. This reduction in the rate at which a person blinks causes a corresponding reduction in the frequency at which the eye is cleansed and bathed by secretions from the glands. Some people aggravate the problem with poor computer position, such as having their computer screens sit above their head. When people look up at a computer screen, it forces their eye lids to open wider, exposing more surface area to the drying air. The foregoing lead to a dry eye syndrome manifested as discomfort, irritation and fatigue. In extreme cases, the irritation can lead to more serious problems affecting the health of the eyes. One factor leading to the reduced blink syndrome is that a video display terminal changes on a micro level as single letters or numbers are added to the screen by an operator. This creates a gradual or micro change to the visual field which will not stimulate a blink response. Furthermore, as we blink, we interrupt our point of gaze, causing the need to refocus and redirect our gaze after each blink, inducing eyestrain. In order to avoid this, we stare, causing dryness.

The present invention overcomes many of the disadvantages inherent in conventional methods and apparatuses for reducing ocular discomfort and vision problems associated with sustained close-range viewing.

SUMMARY OF THE INVENTION

A principal object of the present invention is to provide a system kit and method for use by a viewer to reduce ocular discomfort and vision problems associated with sustained close-range viewing, which overcome the drawbacks of the prior art.

Another object of the present invention is to provide a system kit and a method for use by a viewer to reduce the symptoms and detrimental effects of computer vision syndrome, such as eyestrain, headaches, fatigue, blurring of vision, decreased productivity, dry eyes, progressive increase in the viewer's level of nearsightedness and the like, associated with viewing video display terminals.

Another object of the present invention is to provide a system kit and a method which permit a computer operator to utilize normal or corrected normal vision to perform other tasks at the computer work station while using the system kit and method of the invention to reduce ocular discomfort and vision problems associated with viewing the computer monitor display.

A further object of the present invention is to provide accommodative glasses forming part of the system kit according to the present invention for reducing the amount of accommodation or focusing that the eyes need to do in order to see an object at close range.

A further object of the present invention is to provide visual therapy devices forming part of the system kit according to the present invention which are very simple and inexpensive, and which can be used anywhere without any medical supervision for performing ocular exercises to improve eye muscle control.

An additional object of the present invention is to provide informational displays and record media forming part of the system kit according to the present invention for improving the ergonomic conditions of computer work stations.

A further object of the present invention is to provide a system kit and method for reducing ocular discomfort and vision problems associated with sustained close-range viewing, in combination with a video display terminal, in which the patient viewing the video display terminal has both reduced and relaxed convergence and accommodation.

A further object of the present invention is to provide a system kit and method for reducing ocular discomfort and vision problems associated with sustained close-range viewing which does not need any special knowledge, conditions or measurements, and which can be used with ease by anyone at home or work.

An additional object of the present invention is to provide a system kit for reducing ocular discomfort and vision problems associated with sustained close-range viewing which is very simple to use and inexpensive to manufacture, and a method of using the system kit which is very easy to implement in any place without medical supervision.

The foregoing and other objects of the present invention are carried out by a system kit for reducing ocular discomfort and vision problems associated with sustained close-range viewing of a visual display terminal. The system kit comprises eyewear for reducing the amount of accommodation or focusing required by the eyes of a visual display terminal operator in order to see the visual display terminal at a pre-selected close-range viewing distance, at least one visual therapy device for performing ocular exercises to improve eye muscle control, and information means containing information representing at least information for improving ergonomic conditions while the operator views the visual display terminal and containing instructions on how to use the eyewear and the visual therapy device. The eyewear, the therapy device and the information means, in combination, reduce the operator's ocular discomfort and vision problems associated with sustained viewing of the visual display terminal at the preselected close-range viewing distance.

In one embodiment, the information means comprises an information display having data printed thereon representing the information for improving the ergonomic conditions while viewing the visual display terminal and instructions on how to use the eyewear and the visual therapy devices.

In another embodiment, the information means comprises record media having recorded thereon data representing the information for improving the ergonomic conditions while viewing the visual display terminal and instructions on how to use the eyewear and the visual therapy devices.

In yet another embodiment, the information means comprises both an information display having data printed thereon and a record medium having recorded thereon data representing the information for improving the ergonomic conditions while viewing the visual display terminal and instructions on how to use the eyewear and the visual therapy devices.

The record medium preferably comprises a videotape cassette, a laser disc, a digital video disc, a compact disc, a diskette, a hard drive or other suitable medium.

In another aspect, the present invention is directed to a system for improving visual display terminal operator performance by reducing ocular discomfort and vision problems associated with sustained close-range viewing of the visual display terminal. The system comprises a work station employing a visual display terminal having a luminescent display surface located at a preselected close-range viewing distance from the eyes of an operator of the visual display terminal, eyewear removably positioned before the eyes of the visual display terminal operator for reducing the amount of accommodation or focusing required by the eyes of the operator in order to see the visual display terminal at the preselected close-range viewing distance, at least one visual therapy device for use by the visual display terminal operator to perform ocular exercises to improve eye muscle control, and information means containing information representing at least information for improving ergonomic conditions of the work station and instructions on how to use the eyewear and the visual therapy device. The eyewear, the therapy device and the information means, in combination, reduce the operator's ocular discomfort and vision problems associated with sustained viewing of the visual display terminal at the preselected close-range viewing distance.

In yet another aspect, the present invention is directed to a method for improving visual display terminal operator performance by reducing ocular discomfort and vision problems associated with sustained, close-range viewing of the visual display terminal. The method comprises the steps of removably positioning eyewear before the eyes of an operator while viewing a visual display terminal located in a work station to reduce the amount of accommodation or focusing required by the eyes of the operator in order to see the visual display terminal at a preselected, close-range viewing distance, adjusting ergonomic conditions of the work station to improve visual efficiency of the visual display terminal, and periodically subjecting the visual display terminal operator to at least one visual therapy exercise for performing ocular exercises to improve eye muscle control. The positioning, adjusting and subjecting steps, in combination, reduce the operator's ocular discomfort and vision problems associated with sustained viewing of the visual display terminal at the preselected, close-range viewing distance.

BRIEF DESCRIPTION OF THE DRAWINGS

The foregoing summary, as well as the following detailed description of the preferred embodiments of the invention, will be better understood when read in conjunction with the accompanying drawings. For the purpose of illustrating the invention, there is shown in the drawings an embodiment which is presently preferred. It should be understood, however, that the invention is not limited to the precise arrangement and instrumentalities shown. In the drawings:

FIG. 3A is a fragmentary perspective view showing the Type II glasses in flipped-up position over a pair of conventional eyeglasses, FIG. 3B is a perspective view showing the Type II glasses in flipped-down position, and FIG. 3C is a perspective view, taken from the rear, showing the Type II glasses after removal from the conventional eyeglasses;

FIG. 4A is a fragmentary perspective view showing the Type III glasses in flipped-up position over a pair of conventional eyeglasses, FIG. 4B is a perspective view showing the Type III glasses in flipped-down position, and FIG. 4C is a perspective view, taken from the rear, showing the Type III glasses after removal from the conventional eyeglasses;

FIG. 5 is a schematic view showing one implementation of a part of a method according to the present invention for reducing ocular discomfort and vision problems associated with sustained close-range viewing;

FIG. 6 is a front view of an accommodative rock training device which constitutes part of the system kit according to the present invention;

FIG. 7 is a perspective view showing a patient utilizing the accommodative rock training device of FIG. 6 as part of one visual therapy exercise according to the method of the present invention;

FIG. 8B is cross-sectional view of one embodiment of a visual target for the brock string device, FIG. 8C is a perspective view of another embodiment of the visual target for the brock string device in an unfolded position, FIG. 8D is another embodiment of the brock string device, and FIG. 8E is another embodiment of the visual target for the brock string device.

FIG. 10A is a perspective view and FIG. 10B is a front view of an embodiment of an information display which constitutes part of the system kit according to the present invention;

FIG. 11A is a perspective view of the information display and FIG. 11B is a cross-sectional view taken along line 1—1 of FIG. 11A;

FIG. 15 shows an embodiment of a comfort color determinator chart which constitutes part of the system kit according to the present invention.

DETAILED DESCRIPTION OF THE PREFERRED EMBODIMENTS

While this invention is susceptible of embodiments in many different forms, this specification and the accompanying drawings disclose only preferred embodiments of the invention. The invention is not intended to be limited to the embodiments so described, and the scope of the invention will be pointed out in the appended claims.

For simplicity of description, the preferred embodiments of the invention will be described with reference to a system kit and method for reducing ocular discomfort and vision problems associated with sustained viewing of a computer monitor display. It is understood, however, that the invention is not limited to reducing ocular discomfort and vision problems associated with sustained viewing of computer monitor displays, but rather broadly encompasses the reduction of ocular discomfort and vision problems associated with sustained close-range viewing in general. Likewise, the display is not limited by the embodiments disclosed and may be a television monitor display, a liquid crystal display, a plasma display and any other type of display which causes ocular discomfort and vision problems when viewed at close range for sustained periods of time.

As used herein, the terms "lens" or "lenses" are intended to have their usual and traditional meanings and, in addition, include within their meanings any substantially transparent element, whether or not it refracts light rays. The construction of the lenses and the materials used are well known and will not be described in detail herein.

Figure 1:
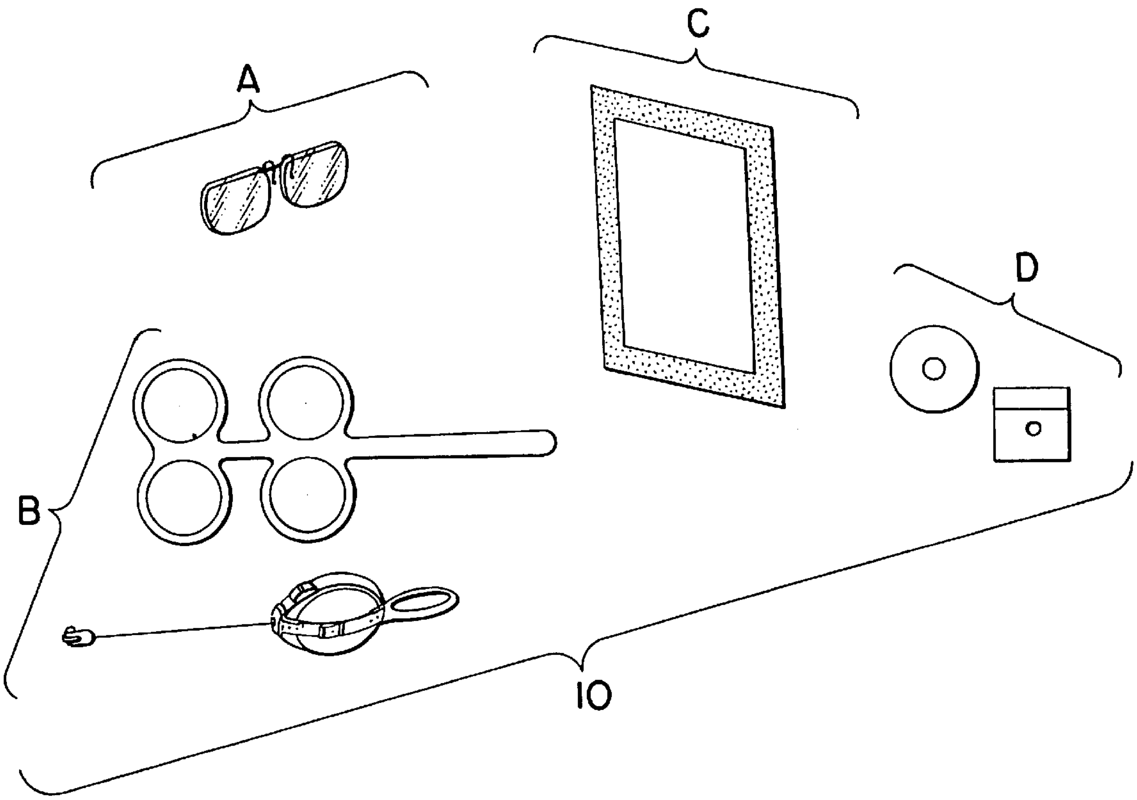
FIG. 1 is a schematic view showing one embodiment of a system kit according to the present invention for reducing ocular discomfort and vision problems associated with sustained close-range viewing.

Referring now to the drawings in detail, wherein like numerals are used to indicate like elements throughout, there is shown in FIGS. 1–15 preferred embodiments of a system kit 10 according to the present invention for reducing ocular discomfort and vision problems associated with sustained close-range viewing. In the preferred embodiment, as shown in FIG. 1, the kit 10 comprises, in combination, eyewear A for reducing the amount of accommodation or focusing that the eye needs to do in order to see an object at close range, visual therapy devices B for performing ocular exercises to improve eye muscle control, and information means C and D containing information representing at least information for improving the ergonomic conditions of computer work stations and instructions on how to use the accommodative glasses and the visual therapy devices to enable the reduction of ocular discomfort and vision problems associated with sustained close-range viewing. As further described below, it will be appreciated by those skilled in the art that the combination of the eyewear A, the visual therapy devices B, and the information means C and D, all of which constitute part of the system kit according to the present invention, provides a new and effective program for computer vision relief. As further described below, optional components of the system kit 10 according to the present invention may include an anti-glare screen for reducing glare/reflections off computer monitor displays, a comfort color determinator chart for selecting the color combination for the computer monitor display which is most comfortable for the user, and/or eye wetting drops for alleviating the discomfort in computer users related to dry eye syndrome.

FIGS. 2, 3A–3C and 4A–4C show preferred embodiments of eyewear according to the present invention for reducing the amount of accommodation or focusing that the eye needs to do in order to see an object at close range. The eyewear comprises three types of accommodative eyeglasses, generally designated at 20, 30 and 50, which constitute part of the system kit according to the present invention. The accommodative eyeglasses 20, 30 and 50 are designed provide clear vision within a range of near and intermediate working distances. More specifically, the accommodative eyeglasses 20, 30 and 50 are designed for viewing displays, such as computer screens, and utilize a specific dioptric power level which reduces the amount of focusing that the eyes must do, thereby reducing the amount of strain. For simplicity of description, the accommodative eyeglasses are hereinafter referred to as Type I glasses 20, Type II glasses 30 and Type III glasses 50.

The kit according to the present invention preferably contains only one of the Type I glasses 20, Type II glasses 30 and Type III glasses 50. The Type I, Type II and Type III glasses are designed to work in conjunction with a user's normal, uncorrected vision or with proper prescription eyewear. A user would select one of the kits according to the present invention which contains either the Type I, Type II or Type III glasses depending on whether the user does not normally require prescription eyewear (i.e., utilizes normal, uncorrected vision), wears contact lenses, wears single vision distance glasses or wears multi-focal lenses (i.e., bifocals or trifocals). Thus, according to the present invention, as further described below, a user who does not normally require prescription eyewear or who wears contact lenses would select the kit containing the Type I glasses 20, a user who wears single vision distance glasses would select the kit containing the Type II eyeglasses 30, and a user who wears bifocals or trifocals would select the kit containing the Type III glasses 50.

Figure 2:
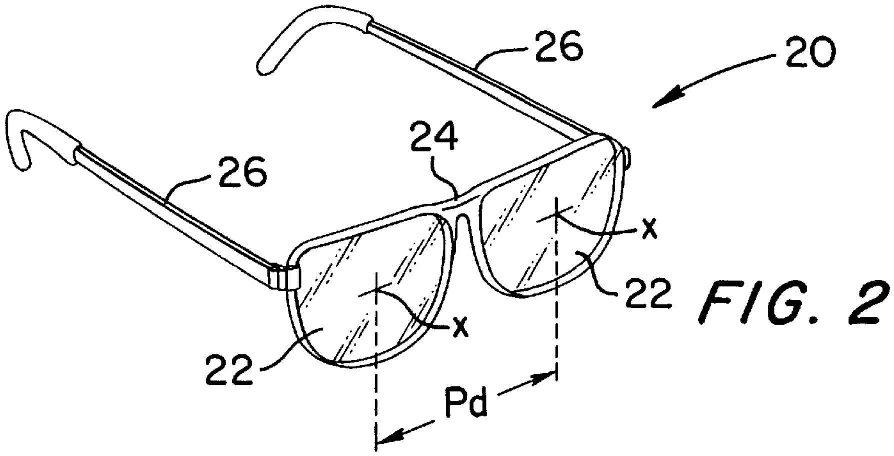
FIG. 2 is a perspective view of a pair of Type I glasses which constitutes part of the system kit according to the present invention.

FIG. 2 is a perspective view of the Type I glasses 20 which are selected by users who do not normally require prescription eyewear (i.e., utilizes normal, uncorrected vision) or who wear contact lenses. The Type I glasses 20 comprise a pair of accommodative lenses 22 provided with a specific dioptric power level which, as further described below, reduces the amount of focusing that the eyes must do in order to see an object at close range. The accommodative lenses 22 are rigidly secured within a conventional ophthalmic frame on opposite sides of a nose bridge piece 24. Each accommodative lens 22 includes an optical center X. A pair of temple bars 26 are provided for supporting the Type I glasses 20 on the wearer's ears.

Figure 3A:
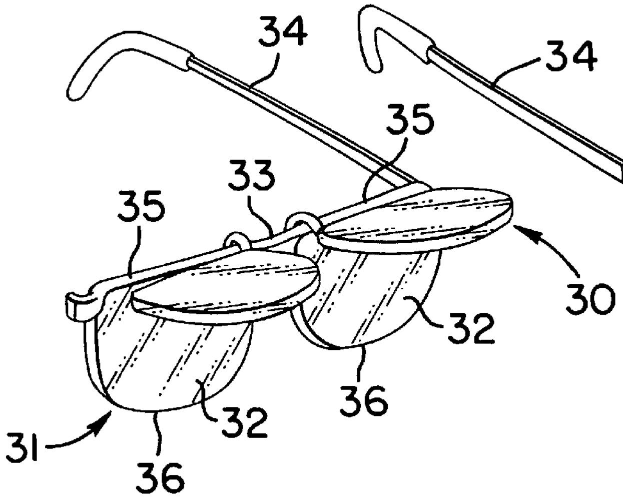
FIGS. 3A–3C are perspective views of a pair of Type II glasses which constitutes part of the system kit according to the present invention, where
Figure 3B:
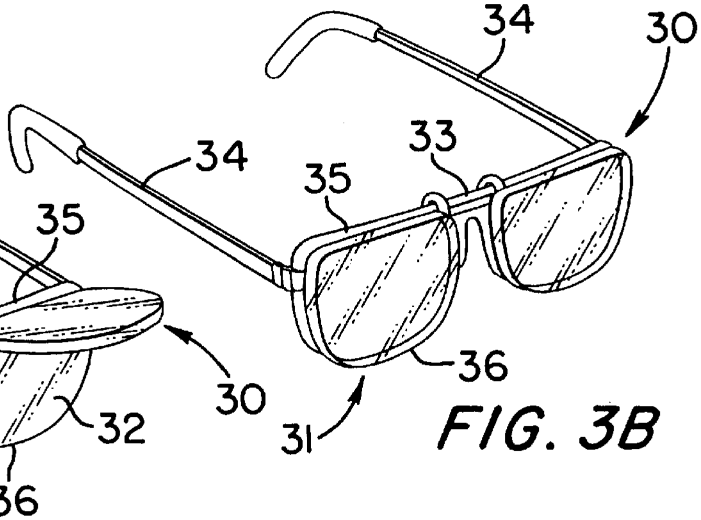
Figure 3C:
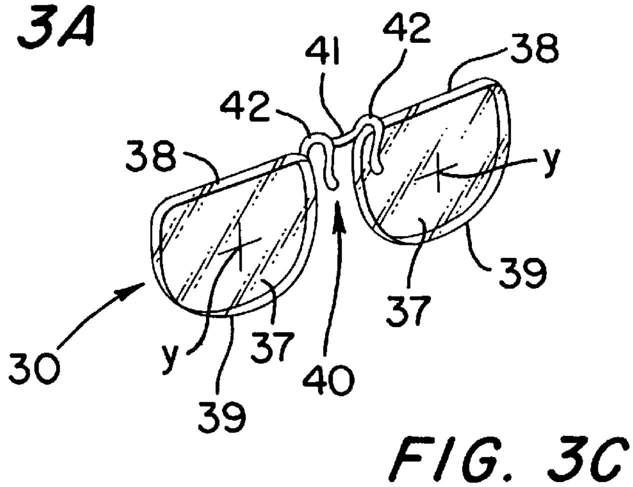

FIGS. 3A–3C are perspective views of the Type II glasses 30 which are selected by users who wear single vision distance eyeglasses, generally designated at 31, which are formed to provide clear vision within a range of near and intermediate working distances. Eyeglasses 31 comprise lenses 32 rigidly secured within a conventional eyeglass frame including a nose bridge-piece 33 and temple bars 34. Each lens 32 includes an upper edge 35 and a lower edge 36.

As shown in FIG. 3C, the Type II glasses 30 comprise a pair of accommodative lenses 37 having an upper edge 38, a lower edge 39, an optical center Y and a specific dioptric power level which, as further described below, reduces the amount of focusing that the eyes must do in order to see an object at close range. The accommodative lenses 37 are mounted on opposite sides of a clip, generally designated at 40, of the type found in commercially available clip-on, flip-up sun glasses. Generally, the clip 40 includes a bridge piece 41 which extends between the accommodative lenses 37, and a pair of hooks 42 for detachably securing the Type II glasses 30 to the upper edges 35 of the eyeglasses 31. The Type II glasses 30 are pivotally coupled to the hooks 42 to allow the accommodative lenses 37 to rotate from a use position overlapping and coacting with the lenses 32 of the eyeglasses 31 (i.e., flipped-down position), as shown in FIG. 3B, to a non-use position out of alignment with the lenses 32 of the eyeglasses 31 (i.e., flipped-up position), as shown in FIG. 3A. When the Type II glasses 30 are in the flipped down position, as shown in FIG. 3B, the upper edges 38 and the lower edges 39 of the accommodative lenses 37 are aligned in close proximity with the upper edges 35 and the lower edges 36, respectively, of the lenses 32.

Figure 4A:
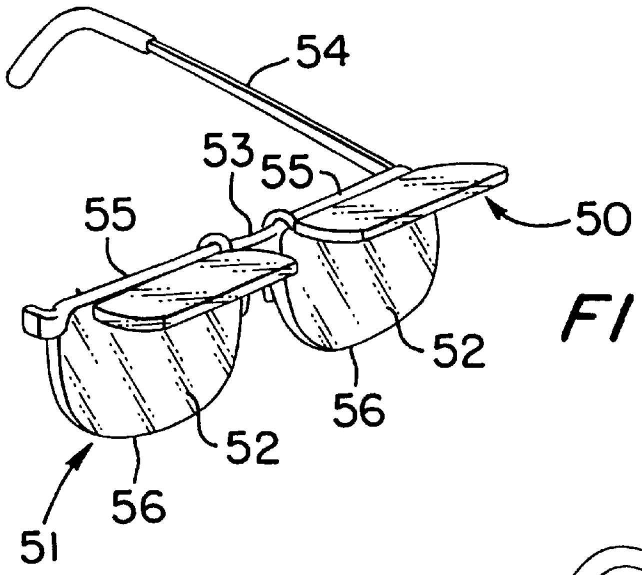
FIGS. 4A–4C are perspective views of a pair of Type III glasses which constitutes part of the system kit according to the present invention, where
Figure 4B:
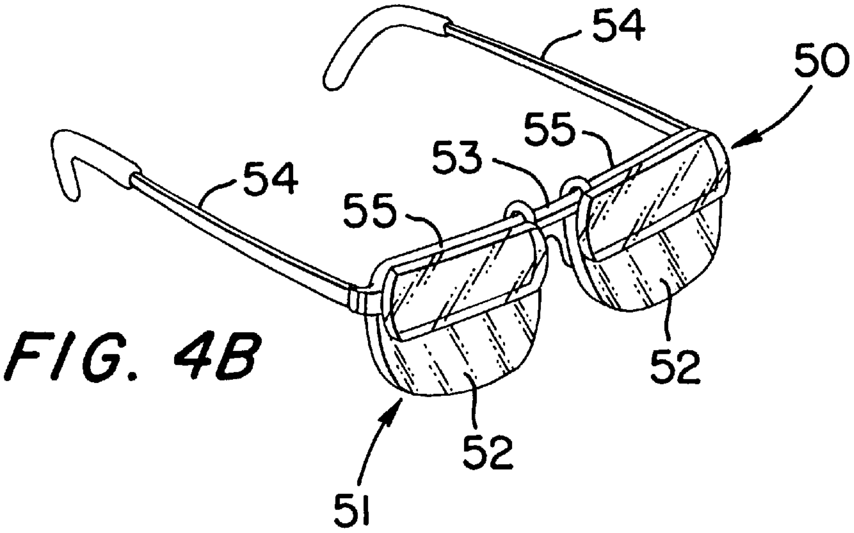
Figure 4C:
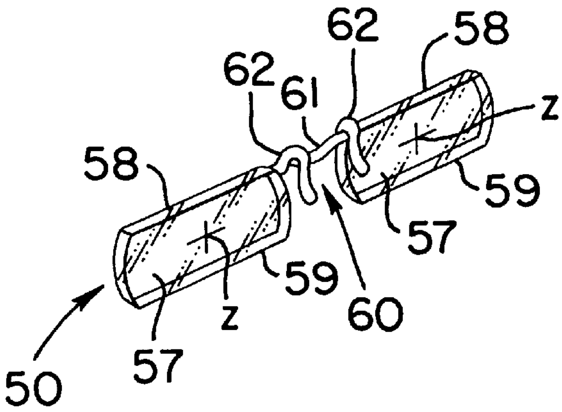

FIGS. 4A–4C are perspective views of the Type III glasses 50 which are selected by users who wear multi-focal eyeglasses, generally designated at 51, such as bifocals having an upper field of vision formed to provide clear vision at long and intermediate distances, and a lower field of vision, formed to provide clear vision within a range of near-point working distances. Eyeglasses 51 comprise lenses 52 rigidly secured within a conventional eyeglass frame including a nose bridgepiece 53 and temple bars 54. Each lens 52 includes an upper edge 55 and a lower edge 56.

As shown in FIG. 4C, the Type III glasses 50 comprise a pair of accommodative lenses 57 having an upper edge 58, a lower edge 59, an optical center Z and a specific dioptric power level which, as further described below, reduces the amount of focusing that the eyes must do in order to see an object at close range. The accommodative lenses 57 are mounted on opposite sides of a clip, generally designated at 60, which is of the conventional type described above for the clip 40 of the Type II glasses 30 and which includes a bridge piece 61 extending between the accommodative lenses 57, and a pair of hooks 62 for detachably securing the Type III glasses 50 to the upper edges 55 of the eyeglasses 51. The Type III glasses 50 are pivotally coupled to the hooks 62 to allow the accommodative lenses 57 to rotate from a use position overlapping and coacting with the upper portion of the lenses 52 of the eyeglasses 51 (i.e., flipped-down position), as shown in FIG. 4B, to a non-use position out of alignment with the lenses 52 of the eyeglasses 51 (i.e., flipped-up position), as shown in FIG. 4A.

When the Type III glasses 50 are in the flipped-down position, as shown in FIG. 4B, the upper edge 58 of each accommodative lens 57 is aligned with a respective upper edge 55 of the lenses 52. The accommodative lenses 57 cover the upper half of lenses 52 and the remainder of the lower half of the accommodative lenses 57 remain uncovered. Thus the Type III glasses 50 make up a pair of "half-glasses" covering only the upper portion of the wearer's field of vision. The lower field of vision of eyeglasses 51 remains uncovered, allowing the wearer to view within the range of near-point working distances, such as for reading books and the like.

The accommodative lenses 22, 37 and 57 of the Type I, Type II and Type III glasses, respectively, are preferably formed of an ophthalmic quality polycarbonate material. However, it will be understood by those of ordinary skill in the art that other materials, such as CR 39, high index plastics, glass and acrylics, are suitable for the accommodative lenses 22, 37 and 57.

Preferably, the pupillary distance Pd of the Type I, Type II and Type III glasses (i.e., the distance between respective centers X, Y and Z of the accommodative lenses) is preset at a distance which would be to the advantage of most people using the glasses forming part of the system kit according to the present invention. For example, since most people have a near pupillary distance between 55 mm and 65 mm (excluding children and midgets), by setting the pupillary distance Pd of the Type I, Type II and Type III glasses at 55 mm, a favorable Base-In prismatic effect is created for most users. A Base-In prism bends light in such a manner such that the user's eyes do not need to turn inward (converge) as much as would be usual if without prismatic effect. This reduces the muscle fatigue and strain which helps reduce CVS.

The specific dioptric power for the accommodative lenses 22, 37 and 57 is selected such that it coacts with the user's normal eyes which don't need correction or with the user's normal eye prescription to focus light closer to the user, thereby reducing the amount of accommodation or focusing that the user's eyes must do in order to see an object which, in turn, reduces eyestrain. As described above, the Type I, Type II and Type III glasses are designed to work in conjunction with a user's normal, uncorrected vision or with normal eye prescription. Thus, in the preferred embodiment of the present invention, the accommodative lenses 22, 37 and 57 are provided with the same dioptric power.

Preferably, the accommodative lenses 22, 37 and 57 are provided with a relatively low plus power selected below about one diopter for working distances in the range of 18–30 inches to enable a computer operator to focus on a computer screen without needing the extent of accommodation otherwise required when no dioptric optical device is used. one diopter is generally defined as the refractive power necessary to focus parallel light rays at one meter. The range of 18–30 inches corresponds to the range of distances over which a computer monitor may typically be located relative to the computer operator. The "working distance" is the distance from the operator's eye position to the screen of the computer monitor. Thus, as shown in FIG. 5, a computer operator wearing eyeglasses 31 and the Type II glasses 30 according to the present invention and who is disposed at a working distance Wd in the range of 18–30 inches can clearly and comfortably view a screen 65 of a computer monitor 66 for sustained periods of time without suffering from the effects of eyestrain.

Preferably, for a working distance in the range of 18–30 inches, the dioptric power of the accommodative lenses 22, 37 and 57 is +0.75 diopter. I have discovered that +0.75 diopter is the optimal power for the accommodative lenses 22, 37 and 57 at the working distance range of 18–30 inches in view of comfort, distortion and depth of focus considerations. The laws of optics dictates that as the power of a lens increases, the depth of focus decreases, the distortions increase and the closer the point of focus becomes. Realistically, this limits the powers which would be optimal and useful for computer users in the range of +0.75 diopter to +1.25 diopters.

I have examined the comfort and effectiveness of the accommodative lenses of the present invention at various dioptric powers and at the working distance range of 18–30 inches using many patients who were experiencing CVS. The use of +1.25 diopter lenses caused numerous complaints relating to distortion. The use of +1.0 diopter lenses exhibited good power for focusing but still elicited some complaints of distortion. The use of weaker, +0.5 diopter lenses did not provide enough focusing help. When I used +0.75 diopter lenses, however, I found that it provided enough focusing help and that there were no complaints about distortion. Thus, at the working distance range of 18–30 inches, the accommodative lenses 22, 37 and 57 having a dioptric power of +0.75 decreases the amount of accommodation required to obtain a clear image of an object (e.g., computer monitor screen) which, in turn, substantially reduces eyestrain. For example, in order to focus on an object at about 24 inches, the viewer needs to focus about +1.50 diopters. When worn by the viewer, the accommodative eyeglasses 20, 30 or 50 (i.e., Type I, Type II or Type III) according to the present invention focus +0.75 of the +1.50 diopters, leaving the eyes of the viewer to focus or accommodate the remaining +0.75, which is easier than focusing the full +1.50 diopters. The focusing of the +0.75 diopters by the accommodative eyeglasses according to the present invention substantially reduces eyestrain, thereby allowing sustained viewing of close-range objects, such as a computer monitor screen, with great comfort and clarity.

As described above, the accommodative glasses 20, 30 and 50 according to the present invention relaxes accommodation of the eyes during sustained close-range viewing of objects. It will be appreciated by those of ordinary skill in the art that, once this accommodation is relaxed, there is an accompanying relaxation of convergence of the eyes. Furthermore, convergence of the eyes is further facilitated by setting the pupillary distance of the accommodative lenses 22, 37 and 57 at 55 mm.

Although a dioptric power of +0.75 is preferred for the accommodative lenses 22, 37 and 57 according to the present invention for sustained close-range viewing (e.g., at working distances of 18–30 inches) due to comfort, distortion and depth of focus considerations, it will be understood by those of ordinary skill in the art that other dioptric powers (e.g., plano to +2.50) are suitable for the accommodative lenses depending on the range of working distance by the user.

Preferably, anti-reflective coatings are added to the front and rear surfaces of the accommodative lenses 22, 37 and 57. Glare and reflections off the monitor is a major source of CVS. There is also some glare from the front and rear surfaces of the accommodative lenses 22, 37 and 57. Anti-reflective coatings reduce glare and reflections, improve light transmission, clarifies images and improve the overall appearance, leading to more comfortable viewing and to a reduction of the symptoms of CVS. As the anti-reflective coating, a coating of magnesium fluoride may be applied very thinly to the accommodative lenses 22, 37 and 57. Other types of anti-reflective coatings may be selected as used in the eyewear industry.

When viewing computer monitor screens, improper room lighting is believed to be the largest single environmental factor contributing to CVS. Dimming room lights to equal the brightness of the monitor screen will improve the room lighting conditions for increased comfort and production by computer users. The accommodative lenses 22, 37 and 57 according to the present invention preferably have a light tint for effectively dimming room lights. A gray tint has been determined to be the best, all-around tint color for different monitor screen colors, including black and white. However, for blue, amber and green monitor screen colors, the optimal tint colors have been determined to be amber, blue and violet, respectively.

Figure 8A:
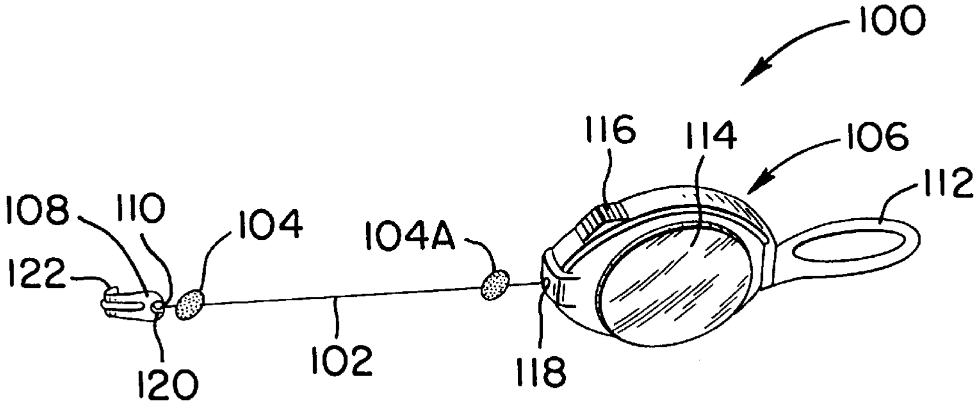
FIGS. 8A–8E show embodiments of a brock string device which constitutes part of the system kit according to the present invention, where 8A is a perspective view of the brock string device showing a string partially retracted from an automatically retracting line dispenser.
Figure 8C:
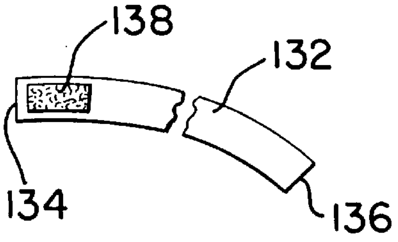
Figure 8B:
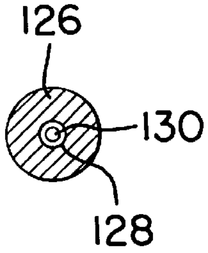
Figure 9:
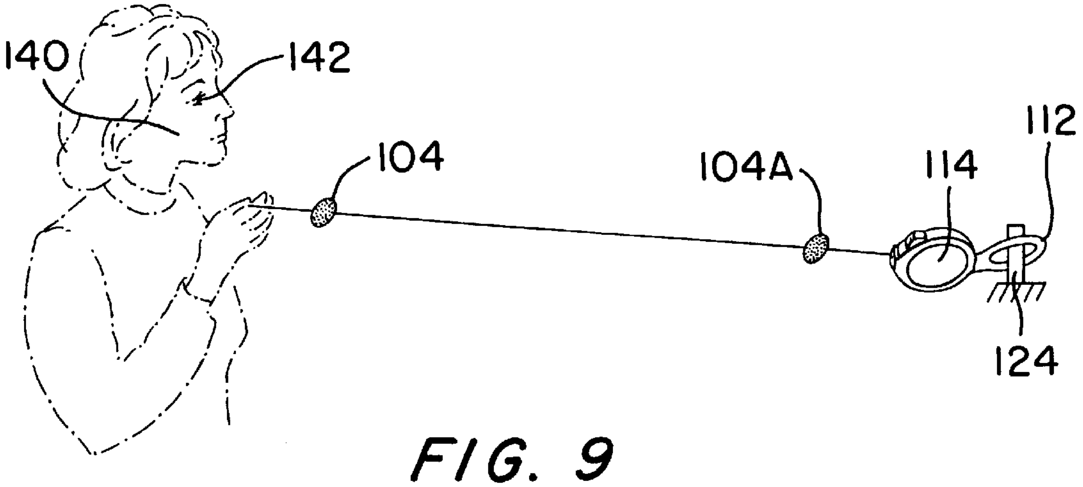
FIG. 9 is a perspective view showing a patient utilizing the brock string device of FIG. 8A as part of another visual therapy exercise according to the method of the present invention.

FIGS. 6–9 show embodiments of visual therapy devices which constitute part of the system kit according to the present invention for performing ocular exercises to improve visual efficiency and decrease the symptoms of CVS. FIGS. 6–7 show an embodiment of an accommodative rock training device 70 (hereinafter referred to as "lens flippers") for improving the strength of the muscles controlling the focusing system of the eyes. FIGS. 8A–9 show embodiments of a physical diplopia cord training device 100 (hereinafter referred to as a "brock string device") for improving the strength of the muscles controlling the pointing of the eyes. The lens flippers 70 and the brock string device 100 can be used at home or at work without any medical supervision.

It will be appreciated by those of ordinary skill in the art that, according to the present invention, the use of the lens flippers 70 and the brock string device 100 for performing ocular exercises to improve eye muscle control, in combination with the accommodative glasses A for reducing the amount of accommodation or focusing that the eye needs to do in order to see an object at close range and, as further described below, the information means C and D containing information for improving the ergonomic conditions of computer work stations and instructions on how to use the accommodative glasses and the visual therapy devices, provide a new and effective system for computer vision relief.

As shown in FIGS. 6 and 7, the lens flippers 70 is an eye exercising device adapted for self-use for stimulating the accommodation of the user's eyes by subjecting the latter to a technique which will fully be described hereinafter. The lens flippers 70 can be used at home or at work without any medical supervision.

The lens flippers comprises a flame having a body 72 which is preferably formed of a hard plastic material and which is symmetrical about a line of symmetry S. The body 72 has a holding portion 74 extending generally along the line of symmetry S, a first pair of lens holders 76, 78 disposed in horizontally spaced relation on one side of the line of symmetry S, a second pair of lens holders 80, 82 disposed in horizontally spaced relation on another side of the line of symmetry S opposite the first side thereof, and a pair of longitudinally extending slots 84, 86 for the reception of the user's nose N in the manner shown in FIG. 7. The vertical slot 84 is disposed between the lens holders 76, 78, and the vertical slot 86 is disposed between the lens holders 80, 82. The lens flippers 70 is provided with a first pair of lenses 88, 90 respectively supported by the lens holders 76, 78, and a second pair of lenses 92, 94 respectively supported by the lens holders 80, 82. The lenses 88, 90, 92 and 94 are respectively centered in the lens holders 76, 78, 80 and 82.

The pupillary distance Pd of the lens flippers 70 is defined as the distance between respective centers O of the first pair of lens holders 76, 78 and the second pair of lens holders 80, 82. Preferably, the pupillary distance Pd of the lens flippers 70 is preset at a generic distance which will not produce any harmful or negative effects. The low dioptric powers used in the lens flippers 70, as further described below, is not strong and will not create strong prismatic effects. In another embodiment, the pupillary distance Pd of the lens flippers 70 is set to correspond to the pupillary distance between the pair of eyes E, E' of the user.

According to the present invention, the first pair of lenses 88, 90 and the second pairs of lenses 92, 94 disposed on opposite sides of the line of symmetry f have respective predetermined positive (+) and negative (–) dioptric powers. For example, in the embodiment of the lens flippers shown in FIG. 6, if the first pair of lenses 88, 90 has a positive dioptric power, the second pair of lenses 92, 94 will have a negative dioptric power. During an eye exercising session using the lens flippers 70, when the user looks at a near object through the second pair of lenses 92, 94 (i.e. negative dioptric power lenses), the user must focus his or her eyes to compensate for the negative dioptric power in order to see the object clearly. In contrast, when the user looks at the same near object through the first pair of lenses 88, 90 (i.e., positive dioptric power lenses), the user must relax his or her focusing system in order to see the object clearly. By alternately subjecting the eyes of the user to the first pair of lenses 88, 90 and the second pair of lenses 92, 94, the muscles of the eyes controlling the focusing system are exercised, thereby improving the strength of the eye muscles which, in turn, improves visual efficiency and decreases the symptoms of CVS.

Preferably, the first pair of lenses 88, 90 (i.e., positive dioptric power lenses) has a stronger positive dioptric power than the negative dioptric power of the second pair of lenses 92, 94 (i.e., negative dioptric power lenses). For example, the first pair of lenses 88, 90 preferably has a dioptric power of +1.50 and the second pair of lenses 92, 94 has a dioptric power of −0.75. The selection of these dioptric powers for the first and second pairs of lenses is a departure from the conventional dioptric powers used for accommodative rock exercises which is typically in the range of ±2.50.

According to the present invention, the selection of a stronger positive dioptric power for the first pair of lenses 88, 90 than the negative dioptric power of the second pair of lenses 92, 94 is specially adapted for computer users, for example, who focus their eyes on a computer screen for extended periods of time and thus have a greater need to relax and unfocus the eyes. Furthermore, a low negative dioptric power for the second pair of lenses 92, 94 is selected so that computer users over 40 years of age, for example, who have diminished focusing ability, can also effectively exercise with the lens flippers 70 to improve the strength of the muscles controlling the focusing system of their eyes.

The body 72, the first pair of lenses 88, 90 and the second pair of lenses 92, 94 are preferably formed separately from a suitable plastic material and then integrated in any desired manner. Alternatively, the body and the first and second pairs of lenses are unitarily molded from a suitable plastic material. It is understood by those of ordinary skill in the art that materials such as ophthalmic quality polycarbonate, CR 39, high index plastics, glass and acrylics, are suitable for the first and second lenses 88, 90, 92 and 94.

When performing the accommodative rock exercise, the lens flippers 70 according to the present invention is always to be used with normal, uncorrected vision or with proper prescription eyewear, including bifocals, reading glasses and contact lenses. For maximum effect in reducing CVS, the accommodative rock exercise is preferably performed while focusing at an object at a distance of 16 to 20 inches from the user's eyes.

During use, the lens flippers 70 is positioned in close proximity to the user's face F with the user's nose N projecting through the longitudinal slot 86, for example, as shown in FIG. 7. When the user's nose N is associated with the longitudinal slot 86 in the manner shown in FIG. 7, the first pair of lenses 88, 90 (i.e., positive dioptric power lenses) is brought into registry with the user's eyes E, E'. With the lens flippers 70 so positioned, the user sights through the first pair of lenses 88, 90 at a near object (e.g., reading material) preferably at a distance of 16 to 20 inches from the user's eyes E, E', and this position of the lens flippers 70 is maintained until such near object is seen clearly. Since the first pair of lenses 88, 90 has a positive dioptric power, as described above, the user can see the near object clearly by relaxing the accommodation to compensate for the positive power. Thereafter, the lens flippers is displaced (i.e., flipped) 180 degrees so that the user's nose N projects through the longitudinal slot 84 and the second pair of lenses 92, 94 (i.e., negative dioptric power lenses) is brought into registry with the user's eyes E, E'. With the lens flippers 70 so positioned, the user sights through the second pair of lenses 92, 94 at the same near object and this position of the lens flippers 70 is maintained until such near object is seen clearly. Since the second pair of lenses 92, 94 has a negative dioptric power, as described above, the user can see the near object clearly by focusing the eyes to compensate for the negative power.

The foregoing procedure of alternately associating the first pair of lenses 88, 90 and the second pair of lenses 92, 94 with the user's eyes is repeated for a predetermined period of time at desired intervals. For example, performing the accommodative rock exercise for five minutes, once or twice daily, will be sufficient to achieve the desired effect. It will be appreciated by those of ordinary skill in the art that a rocking action or effect is achieved by alternately subjecting the user's eyes to the action of the first pair of lenses 88, 90 and the second pair of lenses 92, 94 in the manner described above which stimulates the accommodation of the user's eyes. Thus the lens flippers 70 is operative to stimulate the eyes to improve the strength of the muscles controlling the focusing system of the eyes which, in turn, improves the visual efficiency and decreases the symptoms of CVS.

Referring now to FIGS. 8A–8E and 9, the brock string device 100 is another eye exercising device which forms part of the system kit according to the present invention and which is adapted for self-use for strengthening the pointing muscles of the user's eyes by subjecting the latter to a technique which will fully be described hereinafter. The brock string device 100 can be used at home or at work without any medical supervision.

The brock string device 100 comprises a line, such as a string 102, a pair of visual targets 104, 104A mounted on the string 102, an automatically retracting line dispenser, generally designated at 106, for storing and allowing dispensing and retraction of the string 102, a line catch 108 connected to a distal end portion 110 of the string 102, and an elastic strap 112 connected to the dispenser 106 to facilitate attachment of the dispenser 106 to a fixed surface during use of the brock string device 100.

The dispenser 106 has a casing 114 which houses a conventional line dispensing and retraction mechanism. For example, the conventional line dispensing and retraction mechanism may comprise a spool assembly, a speed regulator assembly and a spool control actuator (not shown) which are typically associated with conventional automatically retracting chalk line dispensers. The spool control actuator preferably comprises a conventional thumb slide assembly which includes a thumb grip 116 slidably mounted on the casing 114 and having a knurled outer surface. The thumb grip 116 is slidable between a neutral position, which allows dispensing or retraction of the string 102, and a locked position, which restricts movement of the string 102. The casing 114 has a string aperture 118 through which the string 102 may travel to be extended and retracted from the dispenser 106 during use of the brock string device 100. The conventional line dispensing and retraction mechanism housed by the casing 114 is incorporated herein by reference and, therefore, further details thereof are omitted.

The distal end portion 110 of the string 102 is connected to the line catch 108 by tying the string 102 through an eyelet 120 thereof. A hook 122 is formed in line catch 108 to facilitate dispensing of the string 102 from the dispenser 106 and retention of the string 102 by the user's hand, as shown in FIG. 9, during use of the brock string device 100. The strap 112 is integrally connected to an end of the dispenser 106 opposite an end thereof having the string aperture 118 from which the string 102 is dispensed and retracted. As shown in FIG. 9, the strap 112 facilitates attachment of the brock string device 100 to a fixed structure 124 or the like during use.

Desirably, the effective length of the string 102 which can be dispensed from the dispenser 106 is in the range of 5 to 20 feet. The effective length of the string 102 is defined as the distance from the distal end portion 110 of the string to the string aperture 118 of the dispenser casing 114. More desirably, the effective length of the string 102 is 10 feet. An effective length of 10 feet for the string 102 has been determined to be especially suitable for effective use of the brock string device 100, particularly during use in confined areas, while allowing the brock string device 100 to be as small in size as possible for convenience of storage during non-use.

The casing 114 and the line catch 108 are preferably formed of a hard, substantially rigid, plastic material, such as polyvinylchloride or a suitable acrylic, or other lightweight, low-friction material. The string 102 is preferably formed of a high-strength fabric material, such as nylon. It is understood, however, that other materials are suitable for the casing 114, the line catch 108, the string 102 and the strap 112 without departing from the spirit and scope of the invention.

The visual targets 104, 104A are positionally adjustable along the length of the string 102. During use of the brock string device 100, as further described below, the visual targets 104, 104A are mounted on the string 102 in spaced-apart relation and proximate the distal end portion 110 of the string 102 and the string aperture 118 of the dispenser casing 114, respectively. The visual targets 104, 104A are visibly distinguishable, preferably by color, to facilitate alternate focusing on the visual targets 104, 104A during use of the brock string device 100. The visual targets 104, 104A are preferably formed of a plastic, fabric or other lightweight, low-friction material.

In one embodiment, as shown in FIG. 8B, each of the visual targets 104, 104A comprises a ball 126 which is generally circular in cross-sectional shape. Each of the balls 126 has a central hole 128 extending therethrough and a sleeve 130 disposed in the hole 128. The sleeves 130 are preferably formed of a plastic material, such as a suitable acrylic, or other lightweight, low-friction material, and are suitably dimensioned to allow the balls 126 to be slid along the string 102 while permitting the balls 126 to remain positioned in place on the string 102 during use of the brock string device 100.

To mount the visual targets 104, 104A on the string 102, a preselected length of the string 102 (e.g., 10 feet) is first dispensed from the dispenser 106 while the thumb grip 116 of the dispenser 106 is in the neutral position, and the thumb grip 116 is then slid to the locked position to restrict movement of the string 102. The distal end portion 110 of the string 102 is then passed through the respective sleeves 130 of the balls 126 prior to tying the distal end 110 of the string 102 through the eyelet 120 of the line catch 108. During use of the brock string device 100, the visual targets 104, 104A are slid to preselected positions along the string 102, as described above, prior to commencing the eye exercise. After completion of the eye exercise, the visual targets 104, 104A are positioned proximate the distal end portion 110 of the string 102 and the string 102 is retracted into the dispenser 106. Thus when the brock string device 100 is stored during non-use, the visual targets 104, 104A remain mounted on the string 102 near the distal end portion 110 thereof.

FIG. 8C is an enlarged view of another embodiment of the visual targets 104, 104A according to the present invention. In this embodiment, each of the visual targets 104, 104A comprises a generally strip-shaped piece of material 132 having opposite end portions 134, 136. The strip-shaped piece of material 132 is provided with suitable connecting means, such as Velcro connector portions 138. It will be understood by those of ordinary skill in the art, however, that other connecting means, such as snap-fit-type connectors or the like, are suitable for connecting the ends 134, 136 of the strip-shaped piece of material 132 to form the visual targets 104, 104A.

To mount the strip-shaped pieces of material 132 on the string 102 to form the visual targets 104, 104A, a preselected length of the string 102 (e.g., 10 feet) is first dispensed from the dispenser 106 while the thumb grip 116 of the dispenser 106 is in the neutral position, and the thumb grip 116 is then slid to the locked position to restrict movement of the string 102. Thereafter, the strip-shaped pieces of material 132 are mounted on the string 102 by means of the Velcro connector portions 138 in spaced-apart relation to form the visual targets 104, 104A. When a user completes the eye exercise using the brock string device 100, the visual targets 104, 104A are positioned proximate the terminal end portion 110 of the string 102 prior to retraction of the string 102 into the dispenser 106 and storage of the brock string device 100. Thus when the brock string device 100 is stored during non-use, the visual targets 104, 104A remain mounted on the string 102 near the distal end portion 110 thereof. Alternatively, the visual targets 104, 104A are removed from the string 102 prior to storing the brock string device 100.

Figure 8D:
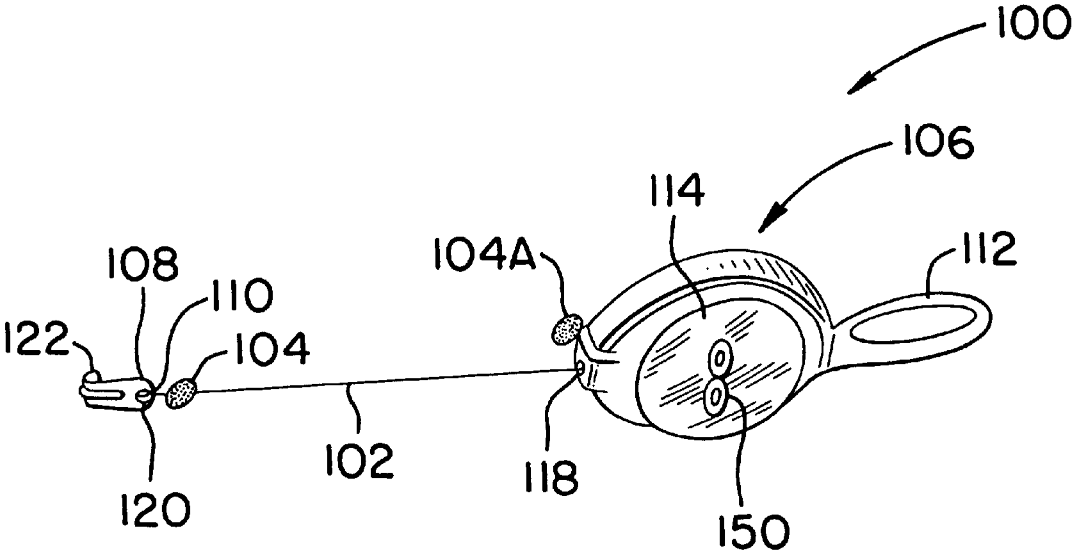

Another embodiment of the brock string device 100 according to the present invention, as shown in FIGS. 8D, SE, comprises all of the components as set forth above for the brock string device of FIG. 8A. However, in the embodiment of FIGS. 8D, 8E, the brock string device 100 comprises a manual, rather than automatic, line dispensing and retraction mechanism 106 having a conventional spool assembly (not shown) housed in the casing 114 and a corresponding conventional lever 150 operably connected to the spool assembly for winding the string 102 around a spool of the spool assembly during retraction of the string 102 into the casing 114. The conventional spool assembly and lever 150 for winding the string 102 are incorporated herein by reference and, therefore, further details thereof are omitted.

Figure 8E:
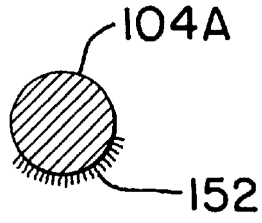
Figure 10A:
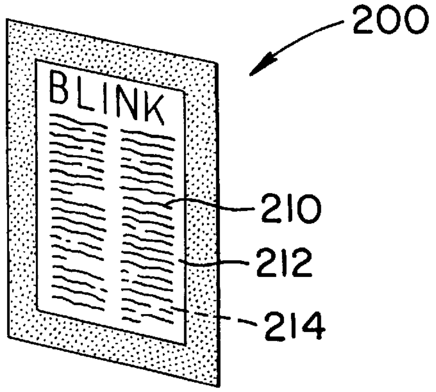

In the embodiment of the brock string device 100 shown in FIG. 8D, the length of the string 102 is desirably in the range of 5 to 20 feet. More desirably, the length of the string 102 is 10 feet as set forth above for the embodiment of FIG. 8A. The visual target 104 preferably comprises the structure of the visual target 104 set forth above for the embodiment of FIG. 8B and is also positioned proximate the distal end portion 110 during use and storage of the brock string device 100. As shown in FIG. 8E, the visual target 104A preferably has a circular cross-sectional shape and is of a solid construction. The visual target 104A is mounted on the casing 114 of the line dispensing and retraction mechanism 106 proximate the string aperture 118 using suitable connecting means. For example, as shown in FIG. 8E, a surface portion of the surface of the visual target 104A may be provided with Velcro connector portions 152 for connection to corresponding mating Velcro connector portions (not shown) provided on a surface portion of the casing 114 proximate the string aperture 118. It will be understood by those of ordinary skill in the art, however, that other connecting means, such an adhesive or snap-fit-type connectors or the like, are suitable for mounting the visual target 104A on the casing 114 of the dispenser 106. The preferred materials for the string 102, the visual targets 104, 104A, the line catch 108 and the casing 114 are as described above for the embodiment of FIGS. 8A, 8B.

In the embodiments shown in FIGS. 8A, 8B, 8D, 8E and 9, the visual targets 104, 104A have a generally circular-shaped cross-section. However, it is understood by those of ordinary skill in the art that other cross-sectional shapes, such as square, rectangular or triangular, are suitable for the visual targets 104, 104A. It is also understood that the manner of mounting the visual targets 104, 104A in the embodiment of the brock string device 100 of FIG. 1D can also be practiced for the embodiment of the brock string device 100 of FIG. 1A, and vice versa.

During use of the brock string device 100 having the automatic line dispensing and retraction mechanism 106, as shown in FIG. 8A, the elastic strap 112 is first attached to a relatively fixed surface 124 as shown in FIG. 9. In this embodiment, for example, the elastic strap 112 is in the form of a loop and is attached to any suitable fixed surface 124, such as a doorknob. A preselected length of the string 102 (e.g., 10 feet) is then dispensed from the dispenser 106 by pulling the string 102 from the hook 122 while the thumb grip 116 of the dispenser 106 is in the neutral position. The thumb grip 116 is then slid to the locked position to restrict movement of the string 102. Prior to dispensing the string 102 from the dispenser 106, the visual targets 104, 104A are positioned proximate the distal end portion 110 of the string 102. After the string 102 is dispensed from the dispenser 106 as set forth above, the visual target 104A is slid along the string 102 to a position proximate the string aperture 118. If one or both of the visual targets 104, 104A comprise a strip-shaped piece of material 132 (FIG. 8C), such visual target or targets are mounted on the string 102 in the manner set forth above for the embodiment of FIG. 8C.

During use of the brock string device 100 having the manual line dispensing and retraction mechanism 106, as shown in FIG. 8D, the elastic strap 112 is also first attached to the fixed surface 124 as shown in FIG. 9. A preselected length of the string 102 (e.g., 10 feet) is then dispensed from the dispenser 106 by pulling the string 102 from the hook 122. Since the visual target 104 is positioned proximate the distal end portion 110 of the string 102 and the visual target 104A is mounted on the casing 114 of the dispenser 106 before the string 102 is dispensed from the dispenser 106, the brock string device 100 is ready for use immediately after dispensing the string 102 from the dispenser 106 without requiring a step for positioning the visual targets 104, 104A to the foregoing positions.

To exercise the eye muscles using the brock string devices 100 of the embodiments of FIGS. 8A an 8D, the user holds the line catch 108 as shown in FIG. 9 so that the visual target 104 proximate the distal end portion 110 of the string 102 is positioned close to the user's face 140 under one of the user's eyes 142. The user then alternates focus between the visual target 104 and the visual target 104A in succession. This alternate focusing procedure is continued for a preselected period of time (e.g., 5 minutes, once or twice per day) to improve the strength of muscles controlling the pointing of the user's eyes 142 which, in turn, improves the visual efficiency and decreases the symptoms of CVS. More specifically, when gaze is changed from the visual target 104 proximate the distal end portion 110 of the string 102 (i.e., the visual target closer to the user's eyes) to the visual target 104A (i.e., the distant visual target), the user's eye muscles which control the pointing of the eyes are exercised in a manner similar to exercising any other muscle of the user's body, such as by toning through repetitive usage. This exercise also trains the muscles which move the eyes to work together as a group more efficiently and more comfortably. Thus, by exercising the eyes using the brock string devices 100 shown in FIGS. 8A and 8D, the user can maintain good muscle tone and coordination, thereby increasing the user's ability to direct the eyes properly.

After completing the eye exercise using the brock string device 100 having the automatic line dispensing and retraction mechanism 106, as shown in FIG. 8A, the user slides the visual targets 104, 104A along the string 102 to positions on the string 102 proximate the distal end portion 110 thereof. Alternatively, if the visual targets 104, 104A are of the type described above with reference to the embodiment of FIG. 8C, the visual targets 104 may be removed from the string 102. Thereafter, the string 102 is allowed to be retracted into the dispenser 106 while the thumb grip 116 is in the neutral position. The brock string device 100 is then stored for future use (e.g., may be left attached to a doorknob by means of the elastic loop 112).

After completing the eye exercise using the brock string device 100 having the manual line dispensing and retraction mechanism 106, as shown in FIG. 8D, the string 102 is retracted into the dispenser 106 by winding the spool assembly (not shown) disposed within the dispenser 106 using the lever 150. The brock string device 100 is then stored for future use (e.g., it may be left attached to a doorknob by means of the elastic loop 112).

The brock string device 100 has been described above with reference to the embodiments of FIGS. 8A and 8D in which an automatic (FIG. 8A) or a manual (FIG. 8D) line dispensing and retraction mechanism 106 is used for storing and allowing dispensing and retraction of the string 102. In an alternative embodiment, the brock string device 100 does not comprise a line dispensing and retraction mechanism, and may simply comprise a predetermined length of the string 102 having the pair of visual targets 104, 104A mounted on the string using any of the mounting methods described above. During use of this alternative embodiment of the brock string device 100, the end of the string 102 opposite the end thereof which is held by the user during the eye exercise is fixed directly to the fixed surface, such as by tying the string to a door knob or the like. The eye exercise for strengthening the pointing muscles of the user's eyes is then performed as described above for the embodiments of the brock string device shown in FIGS. 8A and 8D. After completion of the eye exercise, the string 102 is removed from the fixed surface and simply wound manually and stored for future use.

FIGS. 10–13D show embodiments of information means C and D (FIG. 1) which constitute part of the system kit 10 according to the present invention. As further described below, the information means provide information representing at least information for improving the ergonomic conditions of computer work stations and instructions on how to use the accommodative glasses A and the visual therapy devices B to enable the reduction of ocular discomfort and vision problems associated with sustained close-range viewing. For example, the information may include the environmental factors affecting computer use, including topics such as optimal lighting, proper positioning of the monitors, and numerous other factors which are important for improving visual efficiency and reducing the harmful effects of CVS, and specific instructions for using the accommodative glasses A and visual therapy devices X, including technique and frequency of use.

It will be appreciated by those of ordinary skill in the art that, according to the present invention, the use of the information means c and D, in combination with the visual therapy devices B for performing ocular exercises to improve eye muscle control and the accommodative glasses A for reducing the amount of accommodation or focusing that the eye needs to do in order to see an object at close range, provides a new and effective program for computer vision relief.

Referring now to FIGS. 10A–12B, the information means comprises information displays having data printed thereon representing the information for improving the ergonomic conditions of computer work stations and the instructions on how to use the accommodative glasses and the visual therapy devices. In the embodiment shown in FIG. 10A, the information display comprises an information sheet 200 which includes printed matter and/or indicia 210. The information sheet 200 can be paper with the printed matter and/or indicia 210 thereon, and then lamination placed around the paper, such as clear plastic, for durability and longevity of the information sheet.

The information sheet 200 has surfaces 212, 214. Various information can be located on the surfaces 212, 214. An example of the contents of the information fact sheet 200 according to the present invention is shown in FIG. 10B. For example, with reference to FIG. 10B, the information sheet 200 may contain information on room lighting, glare/reflections, dry eyes, computer position, monitor settings, and tips for reducing CVS, including how-to-use instructions which instruct the user how to use the accommodative glasses A and how to perform ocular exercises using the visual therapy devices B. The information sheet 200 can be placed at or near the other components of the system kit of the present invention or a computer workstation. Preferably, the information sheet 200 can be picked up and reviewed. Alternatively, the information sheet could be posted in a permanent or semi-permanent position at or near the computer workstation.

Thus the function of the information sheet 200 is to provide instructions and guidance for improving the ergonomics of computer use and instructing the user of the system kit how to use the visual therapy devices. Additionally, for example, the term "B L I N K" may be printed at the top of the information sheet 200 in a type set which is readily visible by the user of the system kit. "B L I N K" is intended to remind users to periodically blink in order to reduce discomfort in computer users generally related to "dry eye". In this manner, the rate at which a person blinks during computer use can be effectively increased, thereby resulting in a corresponding increase in the frequency at which the eye is cleansed and bathed by secretions from the tear duct and preventing dry eye syndrome. It is understood, however, that the manner by which a computer operator is reminded to periodically blink for the purpose of reducing discomfort related to "dry eye" may be employed by other than use of the term "B L I N K" printed on the information sheet. For example, the use of any conventional means for creating a conditioning stimulus for stimulating the involuntary reflex blinking of an individual observing a computer terminal monitor is also suitable and is incorporated herein by reference.

Figure 11B:
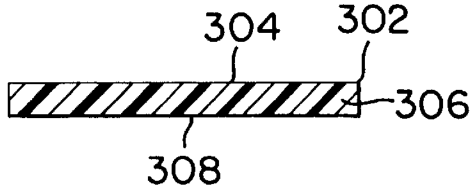
FIGS. 11A–11B show another embodiment of the information display which constitutes part of the system kit according to the present invention, where
Figure 11A:
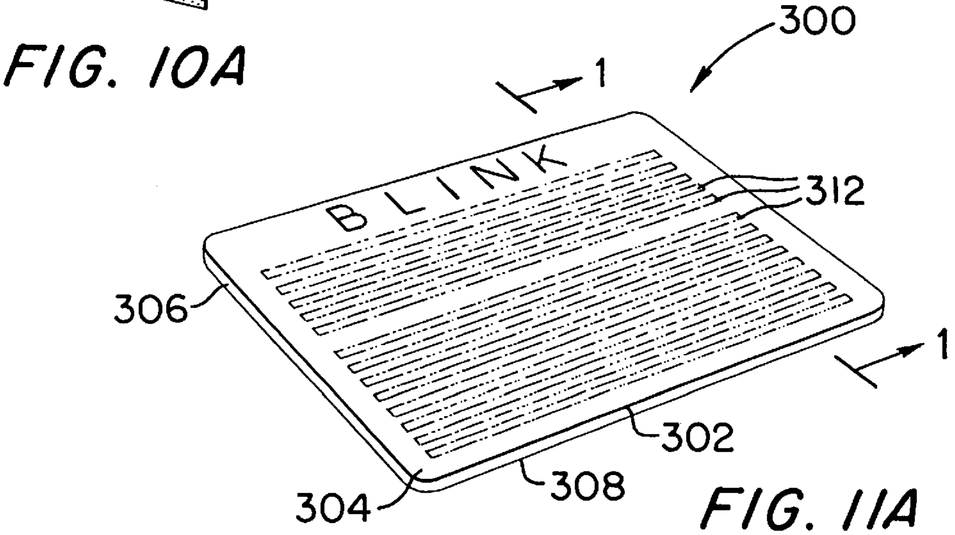

FIGS. 11A–11B show a second embodiment of the information display according to the present invention. The information display comprises an operating pad 300 for the type of computer input device generally referred to as a mouse (hereinafter referred to as a "mouse pad"). The mouse pad 300 includes a control layer 302 having a control surface 304 formed on one side thereof, and an intermediate or support layer 306 supporting the control layer 302 and having a gripping surface 308 on the side opposite the control layer 302. In use, the mouse pad 300 is placed on a work surface, such as the tabletop 310 shown in FIG. 5, with control surface 304 upward. The gripping surface 308 of intermediate layer 306 is thus in contact with the work surface.

According to the present invention, lettering 312 is incorporated into the mouse pad 300 on the control surface 304 as one type of visual display which contains the information, such as facts and/or instructions directed to the ergonomics of computer use and how-to-use instructions for the visual therapy devices, as set forth above for the embodiment of the information display of FIG. 10. The information is printed upon the control surface 304 using methods which are well known in the art.

The material for the control layer 302 is preferably polyvinyl chloride, textured polycarbonates, polystyrene, polyester, or acetate films. The intermediate layer 306 is preferably formed from synthetic rubber, such as neoprene rubber, natural rubber, or vinyl sponge. However, it is understood that other suitable materials known to those skilled in the art can also be used for the control layer 302 and the intermediate layer 306.

The gripping surface 308 comprises a material which allows the intermediate layer 306 to engage the work surface in a non-slip fashion. For example, textures, such as a "cross hatch" texture, can accomplish this purpose, and methods of forming such textures on the gripping surface 308 are well known to those in the art of rubber and plastic fabrication.

Figure 12A:
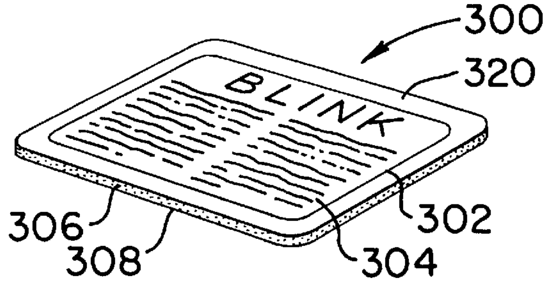
FIGS. 12A and 12B are perspective views of another embodiment of the information display which constitutes part of the system kit according to the present invention.
Figure 12B:
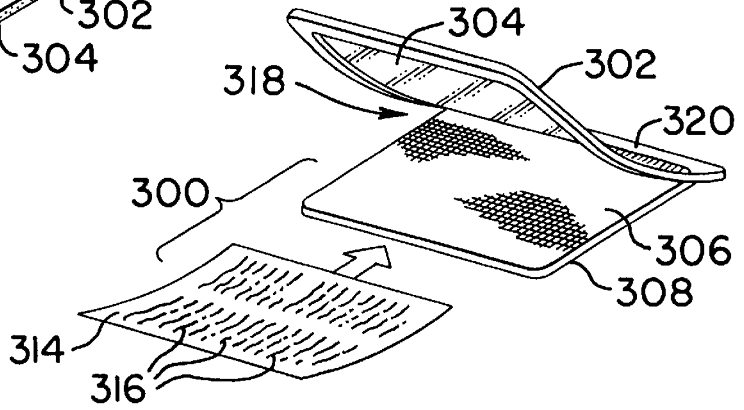

Another embodiment of the information display according to the present invention, as shown in FIGS. 12A–12B, comprises all of the elements set forth above for the embodiment of the information display 300 shown in FIGS. 11A–11B. However, in the embodiment of FIGS. 12A–12B, an information sheet 314, which includes printed matter and/or indicia 316 as set forth above for the information sheet 200 of the embodiment shown in FIG. 10, is placed in a space 318 disposed between the control layer 302 and the intermediate layer 306. The control layer 302 is connected to the intermediate layer 306 along a peripheral edge 320 by an adhesive or other suitable connecting means and can be lifted from the intermediate layer to permit placement of the information sheet 314. The control layer 302 comprises a transparent material in order that the printed matter and/or indicia 316 on the information sheet 314 can be visible. A sheet of transparent polyvinyl chloride or other transparent material suitable to be used as a mouse traveling surface may be used as the transparent material for the control layer 302.

Referring now to FIGS. 13A–13D, the information means in these embodiments comprise record media having recorded thereon data representing information for improving the ergonomic conditions of computer work stations and instructions on how to use the accommodative glasses and the visual therapy devices. In the embodiments shown in FIGS. 13A–13C, the record medium comprises mass storage provided by a floppy disc 400, a CD-ROM disk 410 or a hard disk 420. The floppy disc 400 and the CD-ROM disk 410 are inserted into a diskette drive 405 and into a CD-ROM drive 415, respectively, of a conventional computer (not shown) comprising a central processing unit including a microprocessor, a system random access memory for temporary storage of information and a read only memory for permanent storage of information. The hard disk 420 is part of a fixed disk drive 425 which is connected to a controller of the computerts central processing unit. A display, such as a computer monitor (not shown) is electrically connected to the computer for displaying the information stored in the mass storage 400, 410 or 420.

Figure 13A:
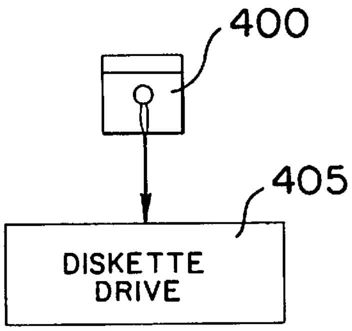
FIGS. 13A–13D are schematic views of embodiments of record media which constitute part of the system kit according to the present invention.
Figure 13B:
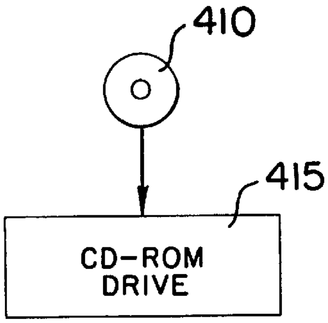
Figure 13C:
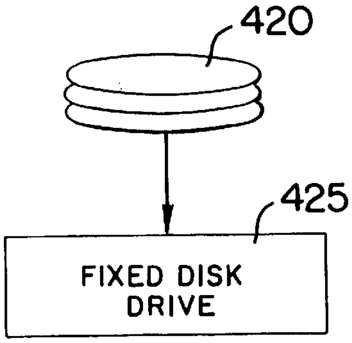
Figure 13D:
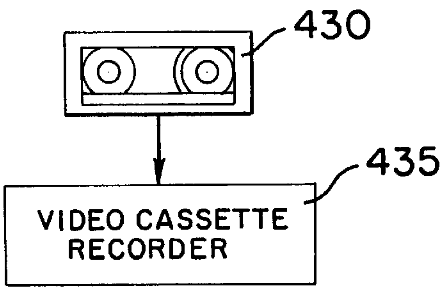

In the embodiment shown in FIG. 13D, the record medium is in the form of a videotape cassette 430. The videotape cassette 430 has a pre-recorded video tape which, during use, is inserted into a video cassette recorder 435 which is electrically connected to a television monitor (not shown) in the customary manner for displaying the contents of pre-recorded information in the videotape cassette.

The record media of the foregoing embodiments shown in FIGS. 13A–13D contain information having audio and/or video portions representing, for example, information for improving the ergonomic conditions of computer work stations and instructions on how to use the accommodative glasses and the visual therapy devices. An example of the contents of the information recorded in the record media is also shown in FIG. 10B.

The record media constituting part of the system kit according to the present invention has been described with reference to embodiments in the form of a videotape cassette and mass storage, such a diskettes, a CD-ROM and a hard drive. However, it is understood by those of ordinary skill in the art that other record media, such as laser discs, digital video discs and compact discs, are suitable for storing the information.

As noted above, the record media forming part of the system kit of the present invention can take various forms depending on the platform of the display. By way of example, if the display is a television monitor, the record medium may be in the form of a videotape cassette, a laser disc, a digital video disc or a compact disc, which would be played by a video cassette recorder, a laser disc player, a digital video disc player or a compact disc player, respectively. In each case, the videotape or disc will have pre-recorded thereon the ergonomic information. In the case of a computer monitor, the record medium may be a floppy disc, a CD-ROM disk or hard disc containing the stored data. In all cases, the record medium is of a type which can be "played" to access the recorded data and convert it to electrical signals for transmission to the processing and drive circuitry of the display. The term "play" is used herein in its broad sense to denote the playing or reading of the record medium to access and read out the data. Thus in the case of a laser disc, a digital video disc or the like, the disc is played by optically reading the disc with a laser, and in the case of a floppy disc, the disc is played by reading out the data stored on the disc.

Figure 14A:
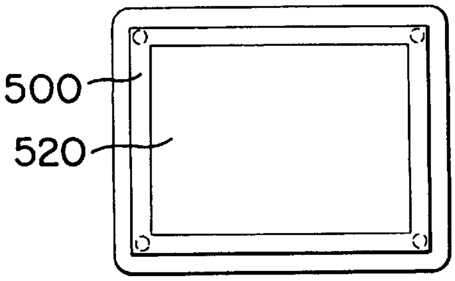
FIGS. 14A and 14B are a front view and a side view, respectively, of an anti-glare screen which constitutes part of the system kit according to the present invention.
Figure 14B:
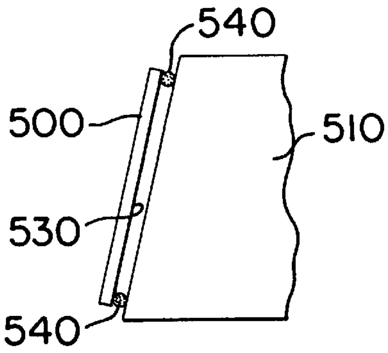

As shown in FIGS. 14A–14B, the system kit according to the present invention may also comprise an anti-glare screen 500 which may be superimposed over the display screen of a monitor 510. Front and rear surfaces 520, 530 of the anti-glare screen 500 are provided with anti-glare coatings, as described above for the anti-glare coatings applied to the surfaces of the accommodative lenses, to reduce glare and reflections off the display screen, to increase contrast and to cut ultraviolet ray emissions from the display screen for more comfortable viewing and to reduce the symptoms of CVS. The construction of the anti-glare screen 500 and its connection to the frame of the monitor 510 using suitable connecting means 540 are conventional and are incorporated herein by reference. Accordingly, further details of the anti-glare screen 500 are omitted.

Referring now to FIG. 15, the system kit according to the present invention may also include a comfort color determinator chart for use in selecting the proper color combination for the letters and background of the computer monitor screen. In the embodiment shown in FIG. 15, the user would initially select five different letter color and background color combinations that seem comfortable to look at. The user then will enter information in the comfort color determinator chart with the five color combinations after using each color combination for a full day. For each color combination, the user will enter his observations as to general comfort (e.g., good, poor, moderate), clarity (e.g., clear, slightly blurred, blurry) and whether the user has experienced headaches. After completing the chart, the user uses the observations entered in the comfort color determinator chart to select which color combination is most comfortable and then sets the selected color combination in the computer.

The comfort color determinator chart may be included in the system kit as a separate sheet of paper. Alternatively, the comfort color determinator chart may be in the form of data stored in any one of the mass storage described above with reference to FIGS. 13A–13C which forms part of the system kit.

The system kit according to the present invention may also include a suitable eye solution for alleviating the discomfort in computer users related to dry eye syndrome. As described in the Background of the Invention, a general eye discomfort in computer users is generally related to "dry eye". The blink rate for computer users can drop from a normal of 12–25 times per minute to 3–5 times per minute. This leads to a dry eye syndrome manifested as discomfort, irritation and fatigue. In extreme cases, the irritation can lead to more serious problems affecting the health of the eyes.

In order to alleviate the discomfort in computer users related to dry eye syndrome, the system kit according to the present invention may include a conventional solution generally known as "artificial tears" or "wetting drops" which is designed to help computer users keep their eyes lubricated. The wetting drops reapply moisture and reduce evaporation, and can be used as needed while using a computer. An example of the wetting drops which constitutes part of the system kit according to the present invention is available from Bausch & Lomb under the trademark COMPUTER EYE DROPS Registered TM.

It will be appreciated by those of ordinary skill in the art that the advantageous effects of the present invention as described herein are obtained by a system kit comprising, in combination, eyewear for reducing the amount of accommodation or focusing that the eye needs to do in order to see an object at close range, visual therapy devices for performing ocular exercises to improve eye muscle control, and information means containing information for improving the ergonomic conditions of computer work stations and instructions on how to use the eyewear and the visual therapy devices. The novel combination of these components in the system kit of the present invention provides a new and effective system for computer vision relief by reducing ocular discomfort and vision problems associated with sustained close-range viewing. The system kit may also include an antiglare screen, a comfort color determinator chart and/or wetting drops for further reducing the effects of computer vision syndrome.

A preferred method for employing the system kit according to the present invention for reducing ocular discomfort and vision problems associated with sustained close-range viewing is herein described.

As described above, the system kit of the present invention contains only one of the Type I glasses 20 (FIG. 2), Type II glasses 30 (FIGS. 3A–3C), and Type III glasses 50 (FIGS. 4A–4C). The Type I, Type II and Type III glasses are designed to work in conjunction with a user's normal, uncorrected vision or with proper prescription eyewear. The user selects one of the system kits according to the present invention which contains either the Type I, Type II or Type III glasses depending on whether the user does not normally require prescription eyewear (i.e., utilizes normal, uncorrected vision), wears contact lenses, wears single vision distance glasses or wears multi-focal lenses (i.e., bifocals or trifocals). Thus, according to the method of the present invention, if the user does not normally require prescription eyewear or wears contact lenses, he/she would select the kit containing the Type I glasses 20. If the user wears single vision distance glasses, he/she would select the kit containing the Type II eyeglasses 30. Likewise, if the user wears bifocals or trifocals, he/she would select the kit containing the Type III glasses 50.

Thus, it will be appreciated by those of ordinary skill in the art that the particular type of accommodative glasses according to the present invention to be selected by a viewer can be determined simply by ascertaining whether the viewer does not normally require prescription eyewear (i.e., utilizes normal, uncorrected vision), wears contact lenses, wears single vision distance glasses or wears multi-focal lens (i.e., bifocals or trifocals). Other factors, such as astigmatism, prisms, and the like need not be considered, since these will either not be applicable for the viewer who utilizes normal, uncorrected vision, or would have already been corrected by the viewer's prescription eyewear. Furthermore, changes in the dioptric power of the accommodative lenses due to variations in the wearer's age are not required since the accommodative lenses in the preferred embodiment of the present invention are provided with the same dioptric power and are designed to work in conjunction with a user's normal, uncorrected vision or with normal eye prescription.

In conjunction with use of the accommodative glasses A for reducing the amount of accommodation or focusing that the user's eye needs to do when viewing a computer screen, the ergonomic conditions of the computer work station are optimized in accordance with the information provided in the information display C and/or record media D (e.g., the ergonomic conditions and how-to-use instructions noted in FIG. 10B). For example, room lighting conditions are optimized and the anti-glare screen is mounted on the computer screen to reduce glare/reflections, the position of the computer monitor is adjusted for comfort, and a comfortable color combination for computer screen is selected in accordance with information obtained from filling out color determinator chart.

In conjunction with use of the accommodative glasses A for reducing the amount of accommodation or focusing that the user's eye needs to do when viewing a computer screen and with the optimization of the ergonomics of the computer work station, the visual therapy devices are used as described above to perform ocular exercises to improve eye muscle control. For example, performing the accommodative rock exercise for five minutes using the lens flippers 70 once or twice daily, will be sufficient to stimulate the eyes to improve the strength of the muscles controlling the focusing system of the eyes. Furthermore, the muscles are exercised using the brock string device 100 for a preselected period of time (e.g., 5 minutes, once or twice per day) to improve the strength of muscles controlling the pointing of the user's eyes. As described above, performing these exercises improves the visual efficiency and decreases the symptoms of CVS.

Moreover, in addition to using the accommodative glasses, improving the ergonomic conditions of the computer work station, and performing the visual therapy exercises as set forth above, the user is reminded to increase the blink rate in order to alleviate discomfort related to dry eye syndrome by viewing the "B L I N K" indicator located on the information display (e.g., information sheet and/or mouse pad) which is placed at or near the computer workstation. Furthermore, using the wetting drops along with increasing the blink rate will enhance the user's eye comfort while viewing the computer screen.

It will be appreciated by those of ordinary skill in the art that the system kit and method according to the present invention overcomes the drawbacks of the conventional art by providing a new and effective system and method for reducing ocular discomfort and vision problems associated with sustained close-range viewing. For example, when used by computer users, the system kit according to the present invention provides an effective program for reducing the effects of computer vision syndrome, including eyestrain associated with sustained viewing of a computer monitor display.

From the foregoing description, it can be seen that the present invention comprises an improved system kit and method for reducing ocular discomfort and vision problems associated with sustained close-range viewing. It will be appreciated by those skilled in the art that obvious changes can be made to the embodiments described in the foregoing description without departing from the broad inventive concept thereof. It is understood, therefore, that this invention is not limited to the particular embodiments disclosed, but is intended to cover all obvious modifications thereof which are within the scope and the spirit of the invention as defined by the appended claims.

What is claimed is:

1. A system kit for reducing ocular discomfort and vision problems of an operator associated with sustained close-range viewing of a visual display terminal, the system kit comprising: an eyewear wearable by the operator for reducing the amount of accommodation or focusing required by the operator's eyes in order to see the visual display terminal at a preselected close-range viewing distance; at least one visual therapy device to enable the operator to perform ocular exercises to improve eye muscle control; and information means containing information representing at least information for improving ergonomic conditions while the operator views the visual display terminal and containing instructions on how to use the eyewear and the visual therapy device; whereby the eyewear, the therapy device and the information means, in combination, reduce the operator's ocular discomfort and vision problems associated with sustained viewing of the visual display terminal at the preselected close-range viewing distance.

2. A system kit according to claim 1; wherein the information means comprises an information display having data printed thereon representing the information for improving ergonomic conditions while the operator views the visual display terminal and containing instructions on how to use the eyewear and the visual therapy device.

3. A system kit according to claim 2; wherein the information display comprises an information sheet having the printed data.

4. A system kit according to claim 2; wherein the information display comprises a mouse operating pad for use on a work surface at a computer work station.

5. A system kit according to claim 4; wherein the mouse operating pad comprises a control layer including a control surface having the printed data, and a support layer for supporting the control layer and having a gripping surface for gripping the work surface at the computer work station.

6. A system kit according to claim 1; wherein the information means comprises a record medium having recorded thereon data representing the information for improving ergonomic conditions while the operator views the visual display terminal and containing instructions on how to use the eyewear and the visual therapy device.

7. A system kit according to claim 6; wherein the record medium comprises at least one of a videotape cassette, a laser disc, a digital video disc, a compact disc, a diskette, and a hard drive.

8. A system kit according to claim 6; wherein the record medium comprises a mass storage device.

9. A system kit according to claim 1; wherein the visual therapy device comprises a frame symmetrical about a line of symmetry, the frame having a holding portion extending generally along the line of symmetry, a first pair of lens holders disposed in horizontally spaced relation on one side of the line of symmetry, a second pair of lens holders disposed in horizontally spaced relation on another side of the line of symmetry opposite the first side thereof, and a pair of slots each dimensioned to receive the operator's nose in one of two different positions of the frame; a first pair of lenses respectively supported by the first pair of lens holders; and a second pair of lenses respectively supported by the second pair of lens holders; wherein during use of the visual therapy device, the operator's eyes register with the first pair of lenses in one of the positions of the frame and register with the second pair of lenses in the other position of the frame.

10. A system kit according to claim 9; wherein the first pair of lenses has a positive dioptric power and the second pair of lenses has a negative dioptric power, the positive dioptric power being stronger than the negative dioptric power.

11. A system kit according to claim 10; wherein the dioptric power of the first pair of lenses is +1.50, and the dioptric power of the second pair of lenses is –0.75.

12. A system kit according to claim 1; wherein the visual therapy device comprises a line having a free end; a dispenser for storing and allowing dispensing and retraction of the line; and a pair of visual targets mounted on respective first and second spaced locations between the dispenser and the free end of the line; wherein when the operator repeatedly alternates focus between the visual target at the first spaced location and the visual target at the second spaced location, the operator's eye muscle control is improved.

13. A system kit according to claim 12; wherein the visual targets are positionably adjustable along the line.

14. A system kit according to claim 12; wherein the first spaced location comprises a portion of the line proximate the free end thereof, and the second spaced location comprises a portion of the dispenser proximate a dispensing end thereof.

15. A system kit according to claim 12; wherein the first spaced location comprises a first portion of the line proximate the free end thereof, and the second spaced location comprises a second portion of the line proximate a dispensing end of the dispenser.

16. A system kit according to claim 12; wherein the visual targets are comprised of a lightweight, low-friction material.

17. A system kit according to claim 12; wherein the visual targets have exterior surfaces of first and second different colors to facilitate alternate focusing on the visual targets during performance of the ocular exercise.

18. A system kit according to claim 1; wherein the at least one visual therapy device comprises a first visual therapy device and a second visual therapy device.

19. A system kit according to claim 18, wherein the first visual therapy device comprises a frame symmetrical about a line of symmetry, the frame having a holding portion extending generally along the line of symmetry, a first pair of lens holders disposed in horizontally spaced relation on one side of the line of symmetry, a second pair of lens holders disposed in horizontally spaced relation on another side of the line of symmetry opposite the first side thereof, and a pair of slots each dimensioned to receive the operator's nose in one of two different positions of the frame; a first pair of lenses respectively supported by the first pair of lens holders; and a second pair of lenses respectively supported by the second pair of lens holders; wherein during use of the visual therapy device, the operator's eyes register with the first pair of lenses in one of the positions of the frame and register with the second pair of lenses in the other position of the frame.

20. A system kit according to claim 19; wherein the second visual therapy device comprises a line having a free end; a dispenser for storing and allowing dispensing and retraction of the line; and a pair of visual targets mounted on respective first and second spaced locations between the dispenser and the free end of the line; wherein when the operator repeatedly alternates focus between the visual target at the first spaced location and the visual target at the second spaced location, the operator's eye muscle control is improved.

21. A system for improving visual display terminal operator performance by reducing ocular discomfort and vision problems associated with sustained close-range viewing of the visual display terminal, the system comprising: a work station employing a visual display terminal having a luminescent display surface located a preselected close-range viewing distance from eyes of an operator of the visual display terminal; eyewear wearable by the visual display terminal operator for reducing the amount of accommodation or focusing required by the eyes of the operator in order to see the visual display terminal at the preselected close-range viewing distance; at least one visual therapy device for use by the visual display terminal operator to perform ocular exercises to improve eye muscle control; and information means containing information representing at least information for adjusting ergonomic conditions of the work station and instructions on how to use the eyewear and the visual therapy device; whereby the eyewear, the therapy device and the information means, in combination, reduce the operator's ocular discomfort and vision problems associated with sustained viewing of the visual display terminal at the preselected close-range viewing distance.

22. A system according to claim 21; wherein the information means comprises an information display having data printed thereon representing the information for improving the ergonomic conditions while viewing the visual terminal monitor and the instructions on how to use the eyewear and the visual therapy devices.

23. A system according to claim 21; wherein the information means comprises a record medium having recorded thereon data representing the information for improving the ergonomic conditions while viewing the visual terminal monitor and the instructions on how to use the eyewear and the visual therapy devices.

24. A system according to claim 23; wherein the record medium comprises at least one of a videotape cassette, a laser disc, a digital video disc, a compact disc, a diskette, and a hard drive.

25. A system according to claim 23; wherein the record medium comprises a mass storage device.

26. A method for improving visual display terminal operator performance by reducing ocular discomfort and vision problems associated with sustained, close-range viewing of a visual display terminal, the method comprising the steps of: removably positioning eyewear on an operator who will be viewing a visual display terminal located in a work station to reduce the amount of accommodation or focusing required by the eyes of the operator in order to see the visual display terminal at a preselected, close-range viewing distance; adjusting ergonomic conditions of the work station to improve visual efficiency of the visual display terminal; and periodically subjecting the visual display terminal operator to at least one visual therapy exercise for performing ocular exercises to improve eye muscle control; whereby the positioning, adjusting and subjecting steps, in combination, reduce the operator's ocular discomfort and vision problems associated with sustained viewing of the visual display terminal at the preselected, close-range viewing distance.

27. A method according to claim 26; wherein the adjusting step comprises adjusting the ergonomic conditions based on information representing at least information for improving the ergonomic conditions while the operator views the visual display terminal.

28. A visual therapy device for use by a user to perform an ocular exercise to improve the user's eye muscle control, the visual therapy device comprising: a frame symmetrical about a line of symmetry, the frame having a holding portion extending generally along the line of symmetry, a first pair of lens holders disposed in horizontally spaced relation on one side of the line of symmetry, a second pair of lens holders disposed in horizontally spaced relation on another side of the line of symmetry opposite the one side thereof, and a pair of clots each dimensioned to receive the operator's nose in one of two different positions of the frame; a first pair of lenses respectively supported by the first pair of lens holders, the first pair of lenses having a positive dioptric power; and a second pair of lenses respectively supported by the second pair of lens holders, the second pair of lenses having a negative dioptric power weaker than the positive dioptric power of the first pair of lenses; wherein during use of the visual therapy device by a user, the user's eyes register with the first pair of lenses in one of the positions of the frame and register with the second pair of lenses in the other position of the frame.

29. A visual therapy device according to claim 28; wherein the dioptric power of the first pair of lenses is +1.50, and the dioptric power of the second pair of lenses is –0.75.

30. A visual therapy device for use by a user to perform an ocular exercise to improve the user's eye muscle control, the visual therapy device comprising: a line having a free end; a dispenser for storing and allowing dispensing and retraction of the line; and a pair of visual targets mounted on respective first and second spaced locations between the dispenser and the free end of the line; wherein when the operator repeatedly alternates focus between the visual target at the first spaced location and the visual target at the second spaced location, the operator's eye muscle control is improved.

31. A visual therapy device according to claim 30; wherein the visual targets are positionably adjustable along the line.

32. A visual therapy device according to claim 30; wherein the first spaced location comprises a portion of the line proximate the free end thereof, and the second spaced location comprises a portion of the dispenser proximate a dispensing end thereof.

33. A visual therapy device according to claim 30; wherein the first spaced location comprises a first portion of the line proximate the free end thereof, and the second spaced location comprises a second portion of the line proximate a dispensing end of the dispenser.

34. A visual therapy device according to claim 30; wherein the visual targets are comprised of a lightweight, low-friction material.

35. A visual therapy device according to claim 30; wherein the visual targets have exterior surfaces of first and second different colors to facilitate alternate focusing on the visual targets during performance of the ocular exercise.

36. A method of performing an ocular exercise by a user to improve the user's eye muscle control, comprising the steps of:

providing a line dispenser which stores and allows dispensing and retraction of a line having a free end;

mounting the dispenser on a fixed structure;

dispensing a preselected length of the line from a dispensing end of the dispenser;

positioning a pair of visual targets on respective first and second spaced locations between the dispenser and the free end of the line;

holding the free end of the line so that the visual target at the first spaced location is positioned close to a user's face under one of the user's eyes; and repeatedly alternating focus between the visual target at the first spaced location and the visual target at the second spaced location to improve the user's eye muscle control.

37. A method according to claim 36; wherein the first spaced location comprises a portion of the line proximate the free end thereof, and the second spaced location comprises a portion of the dispenser proximate the dispensing end thereof.

38. A method according to claim 36; wherein the first spaced location comprises a first portion of the line proximate the free end thereof, and the second spaced location comprises a second portion of the line proximate the dispensing end of the dispenser.

* * * * *